United States Patent
Garner

(10) Patent No.: US 9,145,440 B2
(45) Date of Patent: Sep. 29, 2015

(54) VERSATILE NATIVE CHEMICAL LIGATION TECHNOLOGIES

(71) Applicant: Washington State University, Pullman, WA (US)

(72) Inventor: Philip Garner, Pullman, WA (US)

(73) Assignee: Washington State University, Pullman, WA (US)

(*) Notice: Subject to any disclaimer, the term of this patent is extended or adjusted under 35 U.S.C. 154(b) by 0 days.

(21) Appl. No.: 14/211,176

(22) Filed: Mar. 14, 2014

(65) Prior Publication Data

US 2014/0213758 A1    Jul. 31, 2014

Related U.S. Application Data

(63) Continuation-in-part of application No. 13/675,524, filed on Nov. 13, 2012, now Pat. No. 8,981,049.

(60) Provisional application No. 61/561,520, filed on Nov. 18, 2011.

(51) Int. Cl.
| | |
|---|---|
| *C07K 1/107* | (2006.01) |
| *C07K 1/113* | (2006.01) |
| *C07K 5/00* | (2006.01) |
| *C07K 5/04* | (2006.01) |
| *C07K 5/08* | (2006.01) |
| *C07K 5/083* | (2006.01) |
| *C07H 13/00* | (2006.01) |
| *C07H 13/04* | (2006.01) |

(52) U.S. Cl.
CPC .............. *C07K 1/1077* (2013.01); *C07H 13/04* (2013.01); *C07K 1/107* (2013.01); *C07K 1/1072* (2013.01); *C07K 5/00* (2013.01); *C07K 5/04* (2013.01); *C07K 5/08* (2013.01); *C07K 5/0802* (2013.01); *C07K 5/0804* (2013.01); *C07K 5/0808* (2013.01)

(58) Field of Classification Search
None
See application file for complete search history.

(56) References Cited

PUBLICATIONS

Wang et al., J Am Chem Soc. (Feb. 9, 2011) 133(5), 1597-1602.*
Kimmerlin et al., The Journal of Peptide Research (2005) 65(2), 229-260.*
Jakus et al., Arzneimittelforschung (2001) 51(4), 280-3.*
Rotstein et al.; "Synthesis of peptide macrocycles using unprotected amino aldehydes"; Nature Protocols, vol. 5, No. 11, 2010, pp. 1813-1822.
Galonic et al.; "Aziridin-2-carboxylic Acid-Containing Peptides: Application to Solution- and Solid-Phase Convergent Site-Selective Peptide Modification"; Journal of the American Chemical Society, vol. 127, No. 20, 2005, pp. 7359-7369.
Assem et al.; "Chemoselective Peptidomimetic Ligation Using Thioacid Peptides and Aziridine Templates"; Journal of the American Chemical Society, vol. 132, No. 32, 2010, pp. 10986-10987.
Weiss et al.; "Covalent HLA-B27 / peptide complex induced by specific recognition of an aziridine mimic of arginine"; Proceedings of the National Academy of Science, vol. 93, Oct. 1996, pp. 10945-10948.

* cited by examiner

*Primary Examiner* — Karlheinz R Skowronek
*Assistant Examiner* — Catherine Mader
(74) *Attorney, Agent, or Firm* — Whitham, Curtis, Christofferson & Cook, P.C.

(57) ABSTRACT

Novel methods of native chemical ligation are provided. The methods involve reacting a thioacid (e.g. a peptide thioacid) with an aziridinyl compound (e.g. an aziridinyl peptide) or glycosylamine under mild conditions without the use of protecting groups, and without requiring that a cysteine residue be present in the ligation product. Initial coupling of the thioacid and the aziridinyl compound yields a ligation product containing an aziridinyl ring. Optional subsequent opening of the aziridinyl ring (e.g. via a nucleophilic attack) produces a linearized and modified ligation product. Coupling of a peptide thioacid and glycosylamine yields a glycosylated peptide.

6 Claims, No Drawings

SEQUENCE LISTING

<160> NUMBER OF SEQ ID NOS: 12

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide

```
<220> FEATURE:
<221> NAME/KEY: MISC_FEATURE
<222> LOCATION: (4)..(4)
<223> OTHER INFORMATION: Carboxy terminus is benzylated

<400> SEQUENCE: 1

Lys Tyr Thr Thr
1

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Carboxy terminus is benzylated

<400> SEQUENCE: 2

Glu Tyr Thr Thr
1

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Carboxy terminus is benzylated

<400> SEQUENCE: 3

Cys Tyr Ala Thr
1

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide

<400> SEQUENCE: 4

Lys Tyr Thr Thr Phe Gly
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

Gln Tyr Thr Thr Phe Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

```
<222> LOCATION: (3)..(4)
<223> OTHER INFORMATION: Aziridine is between resideus 3 and 4

<400> SEQUENCE: 6

Lys Tyr Thr Phe Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(4)
<223> OTHER INFORMATION: Aziridine is between residues 3 and 4

<400> SEQUENCE: 7

Glu Tyr Thr Phe Gly
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: carboxyl side chain is sulfated
<220> FEATURE:
<221> NAME/KEY: MISC_FEATURE
<222> LOCATION: (7)..(7)
<223> OTHER INFORMATION: methylated

<400> SEQUENCE: 8

Val Gln Lys Asp Val Thr Ser
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: CARBOHYD
<222> LOCATION: (4)..(4)
<223> OTHER INFORMATION: monosaccharide
<220> FEATURE:
<221> NAME/KEY: MISC_FEATURE
<222> LOCATION: (7)..(7)
<223> OTHER INFORMATION: methylated

<400> SEQUENCE: 9

Val Gln Lys Asn Val Thr Ser
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: CARBOHYD
<222> LOCATION: (4)..(4)
<223> OTHER INFORMATION: monosaccharide
<220> FEATURE:
```

```
<221> NAME/KEY: MISC_FEATURE
<222> LOCATION: (7)..(7)
<223> OTHER INFORMATION: methylated

<400> SEQUENCE: 10

Val Gln Lys Asn Val Thr Ser
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: CARBOHYD
<222> LOCATION: (4)..(4)
<223> OTHER INFORMATION: disaccharide
<220> FEATURE:
<221> NAME/KEY: MISC_FEATURE
<222> LOCATION: (7)..(7)
<223> OTHER INFORMATION: methylated

<400> SEQUENCE: 11

Val Gln Lys Asn Val Thr Ser
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: protected
<220> FEATURE:
<221> NAME/KEY: MISC_FEATURE
<222> LOCATION: (2)..(2)
<223> OTHER INFORMATION: protected
<220> FEATURE:
<221> NAME/KEY: MISC_FEATURE
<222> LOCATION: (3)..(3)
<223> OTHER INFORMATION: protected
<220> FEATURE:
<221> NAME/KEY: MISC_FEATURE
<222> LOCATION: (4)..(4)
<223> OTHER INFORMATION: protected
<220> FEATURE:
<221> NAME/KEY: MISC_FEATURE
<222> LOCATION: (6)..(6)
<223> OTHER INFORMATION: protected
<220> FEATURE:
<221> NAME/KEY: MISC_FEATURE
<222> LOCATION: (7)..(7)
<223> OTHER INFORMATION: protected

<400> SEQUENCE: 12

Val Gln Lys Asp Val Thr Ser
1               5
```

VERSATILE NATIVE CHEMICAL LIGATION TECHNOLOGIES

CROSS-REFERENCE TO RELATED APPLICATIONS

This application is a continuation-in-part of U.S. patent application Ser. No. 13/675,524 filed on Nov. 13, 2012 and claims benefit of U.S. provisional patent application 61/786,146, filed Mar. 14, 2013, the complete contents of both of which is hereby incorporated by reference.

SEQUENCE LISTING

This application includes as the Sequence Listing the complete contents of the accompanying text file "Sequence.txt", created Mar. 12, 2014, containing 4006 bytes, hereby incorporated by reference.

DESCRIPTION

BACKGROUND OF THE INVENTION

1. Field of the Invention

The invention is generally related to forming glycosylated ligation products. In a particular embodiment, a thioacid is reacted with a compound which includes a glycosamine.

2. Background of Invention

The process of native chemical ligation (NCL)[1] involves the chemoselective coupling of unprotected thioesters (Group A) (Group B) via an intramolecular S- to N-acyl transfer to give products of the type A-Cys-B, wherein Cys represents the amino acid residue cysteine.

NCL was a significant achievement because it enabled the synthesis of large peptides and proteins ("protein semisynthesis") under very mild reaction conditions. A key feature of NCL is that it does not require the use of protecting groups and thus represents a particularly powerful approach to specifically modified proteins. The prototypical NCL process is characterized by the chemoselective coupling of "Group A", an unprotected peptide thioester peptide1-Xaa-SR) and a "Group B" amino functionalized compound bearing a branched side chain that includes a removable thiol auxiliary, e.g. an unprotected cysteinyl peptide (H-Cys-peptide2). The resulting ligation product is A-Cys-B, where Cys represents the amino acid residue cysteine. If the reactants are peptides, the ligation product has the general structure peptide1-Xaa-Cys-peptide2.

The rate-determining step for NCL has been shown to be transthioesterification of the peptide thioester by the Cys thiol.[2] Unfortunately, since an N-terminal Cys residue is required,[3] and since the frequency of occurrence of Cys in proteins (1.82%) is low, NCL-based strategies are rather limited, e.g. to ligation at peptide linkages Xaa-Cys, where Xaa is preferably an unhindered amino acid. It follows that the incorporation of post-translationally modified or unnatural amino acids at the ligation site is not generally feasible with NCL.

The lack of generality and coupling efficiency represent significant gaps in the existing NCL technology repertoire.

Shao et al. (Chemistry & Biology 1994 (1) 4:231-234) describe aziridine containing peptides. However, the peptides were synthesized by conventional methods using protecting groups.

Rotstein et al. (Nature Protocols 2010 (5) 11: 1813-22) describe the synthesis of peptides that contain an aziridine ring which can be modified by ring opening. However, the method employs aziridine aldehydes, and the peptides are all macrocyclic and the products do not have a natural peptide backbone.

Weiss et al., (PNAS 1996. 93:10945-10948) describe the synthesis of an azirdine-containing peptide. However, the peptide is an arginine mimic and the aziridine is present on a side chain of the peptide.

Assem et al., (J. Am. Chem. Soc. 2010, 132, 10986-10987), describes chemoselective peptidomimetic ligation using thioacid peptides and aziridine templates. However, the peptide with the aziridine employs protecting groups, and the resulting peptides necessarily contain an SH group, unless removed by a step of desulfurization. Further, the linkage formed is not an alpha-peptide but a beta-peptide.

Galonic et al., (J. Am. Chem. Soc. 2005, 127, 7359-7369), describe aziridine-2-carboxylic acid-containing peptides. However, the synthesis method employs conventional protecting groups, and the aziridine containing peptides were reacted with thiols while they were still protected and attached to the solid phase The covalent union of the carbohydrate and peptide domains of glycoproteins remains a formidable challenge. Recent synthetic approaches to N-linked glycoprotein constructs have generally utilized the native chemical ligation of glycopeptide segments, which are prepared by incorporating the glycosylated amino acids during a solid phase peptide synthesis. Syntheses of N-glycopeptides arising from the coupling of a glycosylamine with an aspartic acid residue embedded in a peptide to give the N-glycosylated peptide have also been reported. Inherent limitations of these protocols necessitate the masking of free amino groups (N-terminus, Lys sidechains) in the peptide, restricting their application to the middle and early stages of a projected glycoprotein synthesis. An aspartylation procedure that circumvents this chemoselectivity issue would permit the introduction of the glycan moiety at a later stage in the synthesis, thus making it more convergent.

Wang et al., (J. Am. Chem. Soc. 2011, 133, 1597-1602), describes the coupling of peptides containing a unique thioacid at the ω-aspartate carboxyl with glycosylamines to give N-linked glycopolypeptides. However, the reaction mechanism involves oxidation of the thioacid to give an active ester intermediate so that the N-terminal and sidechain amines must be protected.

SUMMARY OF THE INVENTION

The present invention provides an improved or modified method of NCL. The method avoids many of the limitations of classical NCL. Like NCL, the present method is carried out under mild conditions and does not require the use of protecting groups. However, the present method advantageously does not require the presence of a cysteinyl peptide for the reaction to occur and is thus not limited to peptides and proteins that contain or can tolerate the presence of a Cys residue. In addition, the method is not unduly sensitive to steric hindrance during the coupling reaction and can be used to produce unprotected peptides that are specifically modified at the ligation site. These features of the method make it applicable for the ligation or coupling of a wide array of molecules, including peptides of any desired sequence, even those that contain non-natural amino acid residues and/or mono, di-, tri- or polysaccharides, and those that contain various types of chemical modifications. The technology thus complements and extends existing native NCL technology.

Accordingly, with reference to Scheme 1, the invention provides methods and compositions for chemical ligation of a first component that includes a thioacid of variable group $R_1$ (1) and a second component that includes a moderately basic (e.g. pKa ranging from about 5.5-6.5) amine functional group. In some aspects, the moderately basic amine is a 3-substituted aziridinyl-2-carbonyl (2, where the 3-substitution is depicted as "$R_2$") to give an aziridinyl-2-$COR_3$-3-$R_2$ ligation product (3). In further aspects, the moderately basic amine is a glycosylamine (Scheme A1), and $R_1$ is, for example, a peptide. This coupling reaction is advantageously promoted by Cu(II) ion. The ligation product 3 has an amide bond at the aziridine nitrogen (or, in the case of ligation product 3', the primary amine of the glycosylamine 2') via which the $R_1$—CO group from the thioacid is attached. Ligation product 3 can be further modified via a nucleophilic attack resulting in an opening of the aziridine ring to yield a linear ligation product 4. Nucleophilic ring-opening is regioselective and stereoselective and results in production of unprotected peptides that are specifically modified at the ligation site.

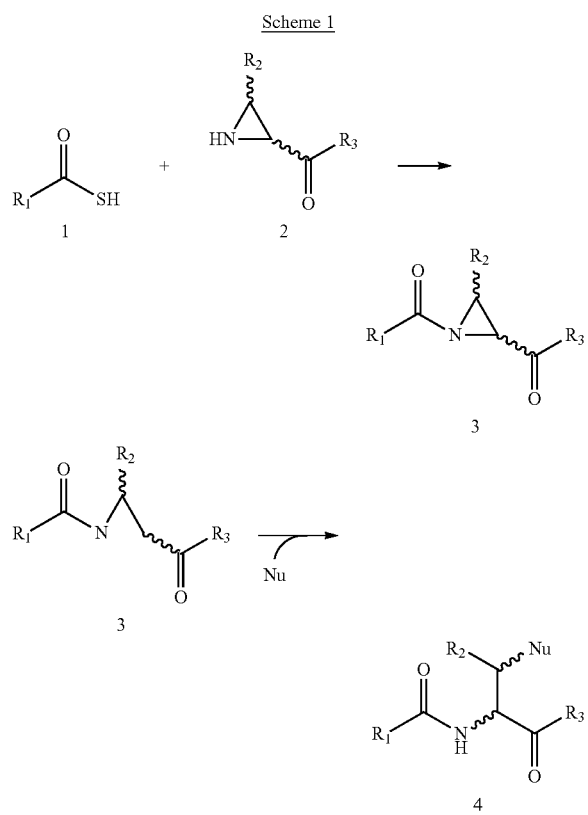

Scheme 1

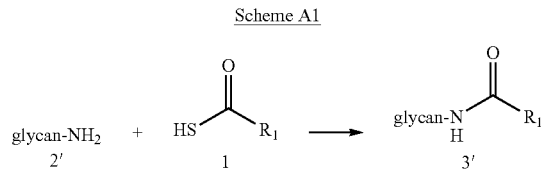

Scheme A1

The methods and compositions described herein are particularly useful for ligation of peptides and polypeptides. Variable groups $R_{1-3}$ can be independently varied as can the glycan, thereby providing the means to produce a wide variety of synthetically assembled complex molecules, including peptides, glycopeptides, and other natural or non-natural amino acid containing peptides. Products produced by the methods disclosed herein, e.g. peptides, glycosylated peptides, etc. are also encompassed by the invention.

The invention thus provides methods of forming a glycosylated ligation product. The methods comprise a step of reacting a thioacid with a compound that comprises a glycosylamine under conditions suitable for forming the ligation product. In some aspects, the conditions suitable for forming the ligation product are such that an amide bond is formed by displacement of SH of the thioacid by N of the glycosylamine, thereby forming the ligation product. The thioacid may be, e.g. a peptide thioacid, and the peptide thioacid may or may not contain a protecting group. The compound that comprises a glycosylamine may be, for example, a monosaccharide, a disaccharide, an oligosaccharide, a polysaccharide or a modified saccharide. In some aspects, the step of reacting is performed in the presence of Cu(II) ion. In yet other aspects, the step of reacting is carried out at ambient temperature.

DETAILED DESCRIPTION

The invention provides methods and compositions for forming a covalent chemical bond between (i.e. for ligating, coupling, joining, etc.) two components of interest (e.g. a first and a second component) to form a polymeric compound. The first component is a thioacid i.e. an organic acid (usually a carboxylic acid) in which one or more of the oxygen atoms have been replaced by sulfur atoms; the thioacid contains a terminal SH that is reactive, i.e. which can undergo chemical coupling reactions. The thioacid also comprises a variable group, $R_1$ in Scheme 1. The second component is a moderately basic (e.g. pKa in the range of from about 5.5 to about 6.5) amine functional group. In certain embodiments the amine is or includes an aziridinyl-2-carbonyl compound that comprises a variable group $R_3$ (see Scheme 1). The aziridinyl ring of component 2 may be further substituted at the 3 position with a second variable group, $R_2$ in Scheme 1. In other embodiments, the amine is attached to a variable glycan (see Scheme 1A).

Reaction between SH of component 1 and the moderately basic amine of component 2 (e.g. mediated by Cu(II) ion) displaces SH from 1 and results in the joining of components 1 and 2 via formation of an amide bond between the organic acid and N of the moderately basic amine.

For embodiments where the moderately basic amine is a glycosylamine, the ligation product comprises an amide bond at the primary amine of the glycosylamine via which the $R_1$—CO group from the thioacid is attached. This type of ligation reaction provides means to synthetically prepare glycosylated peptide sequences wherein the sugar moiety is covalently linked to e.g. either a modified amino acid side chain or the C-terminal carbon.

For embodiments where the moderately basic amine comprises an aziridine ring, the resulting ligation product (3 in Scheme 1) is thus 1-$R_1CO$-2-$COR_3$-$3R_2$-substituted aziridine.

Ligation product 3 can be further modified via opening of the aziridinyl ring which yields a linearized ligation product with formula $R_1CO$—$NHCH(CH(Nu)R_3)CO$—$NHR_2$ (4). In some embodiments, ring opening is accomplished by a nucleophilic attack on carbon at position 3 of the aziridine ring. The nucleophile or a portion thereof is "added" to the carbon, and the bond between positions 1 and 3 of the aziridine ring is broken (see Scheme 1).

In some embodiments, the method involves the coupling of unprotected peptide thioacids and N—H aziridine-2-carbonyl peptides. The unique reactivity of the resulting N-acylated aziridine-2-carbonyl peptides facilitates their subsequent regioselective and stereoselective nucleophilic ring-opening to give unprotected peptides that are specifically modified at the ligation site. Significantly, the overall process is compatible with a variety of unprotected amino acid functionalities, most notably the N-terminus and Lys sidechain, and the method is applicable to both solid and solution phase syntheses, even those involving epimerizable and sterically hindered amino acids.

The following descriptions and definitions are used throughout.

According to the invention, both the joining of components 1 and 2 (and ring opening in the case of aziridinyl peptides) are carried out under mild reaction conditions, precluding the need for protecting groups on variable groups $R_1$-$R_3$. By "mild reaction conditions" we mean ambient temperature (e.g. room temperature, between about 20 to 24° C.). While the use of protecting groups (e.g. 9-fluorenylmethyloxycarbonyl (Fmoc), tert-butyloxycarbonyl (Boc), benzyloxycarbonyl (Cbz or Z), allyloxycarbonyl (alloc), and various lithographic light-cleavable protecting groups, etc.) is not required, in some embodiments it may be desirable to do so for one or more of $R_1$-$R_3$, and such embodiments are also encompassed by the invention.

By "nucleophile" we mean a chemical species that donates an electron-pair to an electrophile to form a chemical bond in a reaction. Because nucleophiles donate electrons, they are by definition Lewis bases. All molecules or ions with a free pair of electrons can act as nucleophiles. Nucleophilic reactions include those in which the nucleophile is an alcohol (alcoholysis), or contains and amino group (aminolysis), etc. Exemplary nucleophiles that may be used in the practice of the invention include but are not limited to: $H_2O$, alcohols, thioacids, thiols, phosphates, halides, isonitriles, and azides, etc.

The term "polymer" means a long molecule consisting of structural units connected by covalent chemical bonds. The units are typically smaller molecules of low to moderate molecular weight (e.g. from about 50 to about 500 Mr), and are linked to each other during a polymerization. The number of structural subunits in a polymer may range from at least 2 to about, for example, 5, 10, 15, 20, 25, 30, 35, 40, 45, 50, 55, 60, 65, 70, 75, 80, 84, 90, 95, or 100 or more (e.g. even up to 500, or up to 1000 or more), per polymer. In some embodiments, the number of structural units will be in the range of from about 2 to about 10, e.g. 2, 3, 4, 5, 6, 7, 8, 9, or 10; or up to about 20, e.g. 11, 12, 13, 14, 15, 16, 17, 18, 19 or 20. The structural units themselves may be "polymers", and may be or may comprise synthetic and/or naturally occurring components. Examples of polymers include, but are not limited to: proteins, nucleic acids, and carbohydrates. One or both of components 1 and 2 may be polymers or structural units of polymers, and the linearized reaction product may be a polymer, and/or may be used as a structural unit of a larger polymer.

As used herein, the term "peptide" refers to two or more amino acids covalently attached through a peptide bond. Peptide is intended to mean both naturally occurring and recombinant forms, as well as other non-naturally occurring forms of the peptide or protein. Peptides may optionally contain a non-natural, or synthetically prepared thioacid on an amino acid side chain or the C-terminal residue.

"Amino acid" as used herein has the usual meaning as understood in the art, e.g. a molecule containing an amine group, a carboxylic acid group and a variable side-chain. Twenty-two "standard" amino acids are known alanine, arginine, aspartic acid, asparagine, cysteine, glycine, glutamic acid, glutamine, histidine, isoleucine, leucine, lysine, methionine, serine, phenyalanine, proline, threonine, tryptophan, tyrosine, valine, as well as selenocysteine, ornithine, etc. Any of these, or any variant thereof (e.g. 5-hydroxytryptophan, L-dihydroxyphenylalanine, phosphorylated amino acids, glycosylated amino acids, lipidated amino acids, dehydroalanine, dehydro-2-aminobutyric acid, lanthionine, methyllanthionine, D-amino acids, amino acids containing any unnatural modification (e.g. azido, alkyne, fluorescent functionality, etc.)) and others, may be employed in the practice of the invention.

The term "alkyl" refers to linear (unbranched) or branched chain unsubstituted hydrocarbon groups of about 1 to 20 carbon atoms, for example. The expression "lower alkyl" refers to unsubstituted alkyl groups of about 1 to 4 carbon atoms.

The term "substituted alkyl" refers to an alkyl group substituted by, for example, about one, two three or four substituents, examples of which include but are not limited to: halo, hydroxy, alkoxy, oxo, alkanoyl, aryloxy, alkanoyloxy, amino, alkylamino, substituted alkylamino, cycloalkylamino, substituted cycloalkylamino, arylamino, substituted arylamino, aralkylamino, substituted aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, is guanidine, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. These substituents may be further substituted, e.g. with alkyl, alkoxy, aryl, aralkyl, etc.

The term "halogen" or "halo" refers to, e.g. fluorine, chlorine, bromine and iodine.

The term "aryl" refers to compounds which contain an aromatic group, e.g. a monocyclic or polycyclic aromatic compound. Monocyclic aryls generally have about 4 to about 7 carbon atoms, bicyclic aryls may have e.g. from about 7 to about 11 carbon atoms, and tricyclic aryls may contain from about 10 to about 15 or more carbon atoms. Exemplary aryls are or comprise groups that include but are not limited to: phenyl, naphthyl, biphenyl (diphenyl), thienyl, indolyl, etc. Aryls may be substituted or unsubstituted, and may or may not include one or more heteroatoms (e.g. S, N, etc.) in one or more ring structures (heteroaryls).

The term "arylalkyl" refers to an aryl or a substituted aryl group bonded directly to an alkyl group, such as benzyl.

The term "substituted aryl" refers to an aryl group substituted by, for example, about one to about four (e.g. 1, 2, 3, or 4) substituents such as alkyl, substituted alkyl, alkenyl, substituted alkenyl, alkynyl, substituted alkynyl, aryl, substituted aryl, aralkyl, halo, trifluoromethoxy, trifluoromethyl, hydroxy, alkoxy, alkanoyl, alkanoyloxy, aryloxy, aralkyloxy, amino, alkylamino, arylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkylsulfonyl, sulfonamido, aryloxy and the like. The substituent may be further substituted by hydroxy, halo, alkyl, alkoxy, alkenyl, alkynyl, aryl or aralkyl.

The term "heteroaryl" or "heteroaromatic" means that the compound is both heterocyclic (containing more than one type of ring, i.e. comprises at least two different rings) and aromatic (at least one of the rings is aromatic as described herein). Such compounds may be substituted or unsubstituted, and may contain heteroatoms within one or more rings, so long as a least one ring of the structure retains its aromatic character. Exemplary heteroaryls and/or components thereof include but are not limited to: pyridine, tetrazole, indazole, etc.

The term "alkenyl" refers to straight or branched chain hydrocarbon groups of about 2 to about 20 carbon atoms, preferably about 2 to about 15 carbon atoms, and most preferably 2 to 8 carbon atoms, having, for example, about one to about four double bonds.

The term "substituted alkenyl" refers to an alkenyl group substituted by, for example, one or more substituents, examples of which include but are not limited to: halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of about 2 to about 20 carbon atoms, preferably about 2 to about 1 carbon atoms, and most preferably about 2 to about 8 carbon atoms, having, for example, about one to about four triple bonds.

The term "substituted alkynyl" refers to an alkynyl group substituted by at least one substituent, examples of which include but are not limited to: halo, hydroxy, alkoxy, alkanoyl alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring system, preferably containing from about 1 to 3 rings with from about 3 to 7 carbons per ring which may be further fused with, for example, one or more unsaturated carbocyclic rings (e.g. a C3-C7 unsaturated rings). Exemplary groups include cyclopropyl, cyclobutyl, cyclopentyl, cyclohexyl, cycloheptyl, and adamantyl. Exemplary substituents include one or more alkyl groups as described above, and/or one or more groups described above as alkyl substituents.

The term "glycosylamine" refers to a mono-, di-, tri-, oligo- or polysaccharide (collectively termed "glycan") containing an amine that is covalently bonded to the anomeric carbon atom of the sugar ring at the reducing end of the saccharide. An oligosaccharide typically contains From about 3 to about 9 sugar (saccharide) units/monomers and a polysaccharide typically contains 10 or more saccharide monomeric units. The saccharide may optionally have additional functional modifications and comprise a "modified saccharide" (e.g. inclusion groups with a specific function such as detection or specific site binding).

A "thioacid" is an organic acid in which one or more of the oxygen atoms have been replaced by sulfur atoms.

The terms "heterocycle", "heterocyclic" and "heterocyclyl" refer to an optionally substituted, fully saturated or unsaturated, aromatic or nonaromatic cyclic group which, for example, is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

The term "heteroatoms" shall include at least oxygen, sulfur and nitrogen.

The compounds of the invention may form salts which are also within the scope of this invention. Pharmaceutically acceptable (i.e. non-toxic, physiologically acceptable) salts are preferred, although other salts are also useful, e.g., in isolating or purifying the compounds of this invention.

An embodiment of the invention is directed to methods and compositions for chemical ligation of a first component that includes a thioacid 1 and a second component selected from i) a 3-substituted or 3-unsubstituted aziridinyl-2-carbonyl component 2 or ii) a glycosylamine S to give the ligation products 3 and 6, respectively, having an amide bond at the ligation site (Scheme 1 and Scheme 1A). In some embodiments, the ligation is promoted by Cu(II) ions. However, this need not always be the case, as other catalysts may be discovered and/or employed.

The ligation product 3 (optionally) can be further converted via ring opening (e.g. by nucleophillic attack) to yield ligation product 4. (Scheme 1) Groups $R_{1-3}$, can be independently varied, thereby providing means to synthetically assemble various types of polymers and/or oligomers, including peptides, polypeptides, and various other natural or non-naturally occurring amino acid containing polymers. In one embodiment, $R_1$ and $R_3$ comprise amino acids or peptides the identity or primary sequences of which may be varied independently. In certain embodiments, $R_1$, $R_2$ and/or $R_3$ may comprise a polymer. In certain embodiments $R_1$, $R_2$ and/or $R_3$ may comprise a hydrogen (e.g. R=H), alkyl, substituted alkyl, halogen, aryl, aralkyl, substituted aryl, heteroaryl, alkenyl, substituted alkenyl, alkynyl, substituted alkynyl, cycloalkyl, heterocycle or heteroatom. In certain embodiments, $R_2$ comprises a chemical group suitable to form an amino acid side chain upon ring opening. In certain embodiments the $R_2$ may comprise a biologically active agent, examples include but are not limited to: a sugar, glycan, carbohydrate, nucleotide, nucleic acid, cofactor, peptide, prodrug, polymer, and/or lipid. In yet further embodiments $R_1$, $R_2$ and or $R_3$ may comprise a group operable for the detection or identification of the ligation product (i.e. they may be or comprise a detectable label), examples of which include but are not limited to: a fluorescent agent, a colored agent, a radiolabel, a capture agent (e.g. biotin), and/or a detectable polymer.

In certain embodiments, it may be desirable to open (break) the aziridine ring of compound 3, i.e. to linearize the molecule (although this is not always the case, since in some embodiments the desired end product may be "intermediate" 3 of Scheme 1). If desired, ring opening may be accomplished by a variety of mechanisms, including but not limited to, for example: isomerization (to yield a dehydroamino acid residue), and ring opening by exposing compound 3 to a suitable nucleophile. The nucleophile (Nu) may comprise a chemical group suitable to form an amino acid side chain upon ring opening. In certain embodiments the nucleophile (Nu) may comprise a biologically active agent, examples of which include but are not limited to: a sugar, glycan, carbohydrate, nucleotide, nucleic acid, cofactor, peptide, prodrug, radioactive agent, polymer, thioacid, thiol, phosphoric acid, azide, and/or isocyanide. In yet further embodiments, the nucleophile (Nu) may comprise a group operable, functioning or suitable for the detection or identification of the ligation product, examples of which include but are not limited to: a fluorescent agent, a colored agent, radiolabel, and/or a capture agent (e.g. biotin). In other embodiments, the nucleophile may comprise a chemical group which it is advantageous to include or retain in the final product. For example, Nu may comprise a thiopalmitic acid to give a specifically S-palmitoylated product or the Nu may comprise a ubiquitin thioacid to give a specifically S-ubiquitinated product.

In some embodiments, the ligation reaction is carried out using a single type of thioacid and a single type of aziridine compound. However, this need not always be the case. In some embodiments, multiple types of thioacids may be reacted with one aziridine compound in a reaction, or with multiple types of aziridine compounds, or multiple types of aziridine compounds may be reacted with one type of thioacid or with multiple types of thioacids, so that a mixture of reaction products is produced.

Scheme 2 provides an overview of the utility of the present invention with respect to the many variations that can be introduced into the composition of compounds synthesized by the method. Depending on the reaction conditions and specific nature of the nucleophile, a variety of distinct ligation products can be formed. Here $R_4$, $R_5$, $R_6$ and $R_7$ are independently selected from hydrogen (e.g. R=H), alkyl, substituted alkyl, halogen, aryl, aralkyl, substituted aryl, heteroaryl, alkenyl, substituted alkenyl, alkynyl, substituted alkynyl, cycloalkyl, heterocycle or heteroatom. X is a heteroatom present on $R_3$ prior to the opening of the aziridine ring.

Embodiments of the invention are further illustrated by the foregoing Examples, which should not be interpreted as limiting the invention in any way.

EXAMPLES

Example 1

Aziridine-Mediated Ligation and Site-Specific Modification of Unprotected Peptides Native chemical ligation (NCL)[1] enables the convergent synthesis of peptides and proteins under mild reaction conditions without the need for protecting groups. The NCL process is characterized by the chemoselective coupling of unprotected peptide thioesters (peptide1-Xaa-SR) and unprotected cysteinyl peptides (H-Cys-peptide2) to give ligation products peptide1-Xaa-Cys-peptide[2]. Since an N-terminal Cys residue is required,[2] the general application of NCL to peptide/protein synthesis is limited to ligation at peptide linkages Xaa-Cys, where Xaa is preferably an unhindered amino acid. It follows that the incorporation of post-translationally modified or unnatural amino acids at the ligation site is not feasible with NCL.

We now disclose a ligation protocol that combines the convergent synthesis of unprotected aziridine-2-carbonyl containing peptides with their controlled site-specific chemical modification. The key reaction (Scheme 1) involves chemoselective Cu(II)-promoted coupling of a peptide thioacid[3] 1 with an aziridine-2-carbonyl (Azy) peptide 2 to give the initial ligation product 3 under native conditions. The unique properties of the chemical species involved—a moderately acidic thioacid combined with a moderately basic aziridine—enable the aziridine-mediated peptide ligation to be performed without to peptide protecting groups. The Azy-containing peptide 3 may be converted to a site-specifically

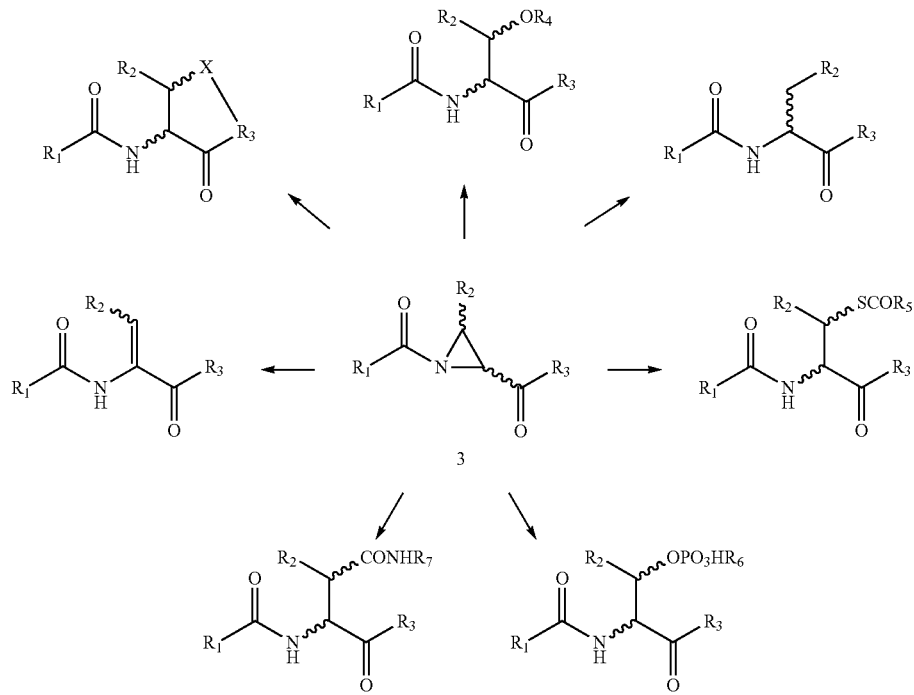

Scheme 2 modified peptide 4 through regioselective opening of the aziridine ring by a nucleophile. Modifications may be introduced via the aziridine substituent ("R") and/or the nucleophilic species ("Nu").

The potential utility of using an aziridine embedded in the backbone of a peptide as an electrophilic handle for the site-specific introduction of modifications has been recognized for some time.[4,5,6] However, the difficulty associated with the synthesis and manipulation of unprotected Azy-containing peptides has limited the full exploration and exploitation of their properties. In this communication, the aziridine-mediated peptide ligation concept is illustrated with a methyl-substituted aziridine-2-carbonyl moiety using water as the nucleophile, with the net result being ligation at a threonine site.

Our study began with thioacetic acid (5) serving as a model for 1 and the known[6] aziridine H-Azy(Me)-NHBn (6, Azy(Me)=(2S,3S)3-methylaziridine-2-carbonyl) as a model for 2. In the presence of $Cu(OAc)_2 \cdot H_2O$, thioacid 5 reacted rapidly with aziridine 6 in mixtures of DMF and phosphate-citrate buffer (pH range 4.2-7.2) to give Ac-Azy(Me)-NHBn (7, corresponding to structure 3 in Scheme 1). Stoichiometric Cu(II) was found to be essential for clean and efficient coupling. In its absence, a complex mixture of products was observed, emanating from non-regioselective ring opening of 6 by 5 and, presumably, S- to N-acyl transfer.[8,9] The use of AgOAc instead of $Cu(OAc)_2 \cdot H_2O$ resulted in a much slower reaction.[10] The subpar performance with $K_3Fe(CN)_6$ suggested that the Cu(II)-mediated reaction does not simply involve an oxidative mechanism.[11] These experiments established the critical role that Cu(II) plays in the aziridine-mediated coupling process as well as the reaction's compatibility with aqueous conditions.

The next stage of reaction optimization focused on assessing the level of epimerization during the coupling of Ac-Phe-SH (8)[12] to 6 and defining conditions to minimize it (Table 1). This coupling reaction proceeded rapidly and cleanly in DMF-aqueous buffers to produce Ac-Phe-Azy(Me)-NHBn (9). However, 13-14% of the epimeric product Ac-phe-Azy(Me)-NHBn (epi-9) was also observed in these reactions (Entries 1-3). The level of epimerization could be reduced to 6% when the reaction was performed in DMF alone but the crude yield was lowered (Entry 4). The inclusion of 1-hydroxybenzotriazole (HOBt) in the reaction mixture was found to reduce the level of epimerization to 10% in DMF-aqueous buffer and 5% in DMF. HOBt also increased the yield of the ligation reaction. The optimal coupling conditions were thus defined as 1 equiv of $Cu(OAc)_2 \cdot H_2O$ and 2 equiv HOBt in DMF.

TABLE 1

Optimization of Coupling Reaction Conditions

| Entry | Solvent | HOBt (equiv) | 9 + epi-9 (% yield) | epi-9 [1](mol %) |
|---|---|---|---|---|
| 1 | 1:1 DMF-buffer (pH 7.2) | 0 | 68 | 13 |
| 2 | 1:1 DMF-buffer (pH 6.2) | 0 | 82 | 13 |
| 3 | 1:1 DMF-buffer (pH 5.2) | 0 | 87 | 14 |
| 4 | DMF | 0 | 53 | 6 |
| 5 | 1:1 DMF-buffer (pH 7.2) | 2 | 88 | 10 |
| 6 | DMF | 2 | 89 | 5 |

We were now ready to combine the coupling reaction with an aziridine ring-opening reaction and address the chemoselectivity issue (Table 2). It was decided to use $H_2O$ as the nucleophile converting the unprotected Azy(Me)-containing peptide to a Thr-containing peptide (10+11→[12]→13). First, the coupling of 8 and 6 was repeated but, rather than isolate 9, the reaction mixture was treated directly with 10% TFA/$H_2O$. The hydrolysis product Ac-Phe-Thr-NHBn (14) was isolated in good overall yield after standard workup and purification (Entry 1).[13] The formation of this 14 is consistent with regioselective and stereoselective nucleophilic opening of the aziridine ring at C3 by $H_2O$. The reaction of diastereomerically pure dipeptide thioacid Fmoc-Phe-Ala-SH (15) and aziridine 6 produced Fmoc-Phe-Ala-Thr-NHBn (16) (Entry 2).[14] Comparison with an authentic sample of Fmoc-Phe-Ala-Thr-NHBn (epi-16) established the level of epimerization at 5%.

TABLE 2

Aziridine-Mediated Peptide Ligation at Xaa-Thr Sites

| Entry | Thioacid (1.1 equiv.) | Aziridine | Solvent | Product | Yield |
|---|---|---|---|---|---|
| 1 | Ac-Phe-SH (8) | H-Azy(Me)—NHBn (6) | DMF | Ac-Phe-Thr-NHBn (14) | 69 |
| 2 | Fmoc-Phe-Ala-SH (15) | H-Azy(Me)—NHBn (6) | DMF | Fmoc-Phe-Ala-Thr-NHBn (16) | 72 |
| 3 | H-Lys-Tyr-Thr-SH (17) | H-Azy(Me)—NHBn (6) | DMF | H-Lys-Tyr-Thr-Thr-NHBn (18) (SEQ ID NO: 1) | 80 |
| 4 | H-Glu-Tyr-Thr-SH (19) | H-Azy(Me)—NHBn (6) | DMF | H-Glu-Tyr-Thr-Thr-NHBn (20) (SEQ ID NO: 2) | 69 |
| 5 | H-Glu-Tyr-Thr-SH (19) | H-Azy(Me)—NHBn (6) | 0.2M Pi-citrate buffer, pH 6.9 | H-Glu-Tyr-Thr-Thr-NHBn (20) (SEQ ID NO: 2) | 71 |
| 6 | H-Glu-Tyr-Thr-SH (19) | H-Azy(Me)—NHBn (6) | 8M urea in 0.1M Pi buffer, pH 7.5 | H-Glu-Tyr-Thr-Thr-NHBn (20) (SEQ ID NO: 2) | 88 |
| 7 | H-Cys-Tyr-Ala-SH (21) | H-Azy(Me)—NHBn (6) | DMF | H-Cys-Tyr-Ala-Thr-NHBn (22) (SEQ ID NO: 3) (H-Cys-Tyr-Ala-Thr-NHBn)$_2$ (23) (SEQ ID NO: 3) | 43 40 |
| 8 | H-Lys-Tyr-Thr-SH (17) | H-Azy(Me)-Phe-Gly-NH$_2$ (24) | DMF | H-Lys-Tyr-Thr-Thr-Phe-Gly-NH$_2$ (25)(SEQ ID NO: 4) | 78 |
| 9 | H-Glu-Tyr-Thr-SH (19) | H-Azy(Me)-Phe-Gly-NH$_2$ (24) | 8M urea in 0.1M Pi buffer, pH 7.5 | H-Glu-Tyr-Thr-Thr-Phe-Gly-NH$_2$ (26) (SEQ ID NO: 5) | 77 |

The coupling/ring-opening sequence was then performed with H-Lys-Tyr-Thr-SH (17)[15] and 6 to produce H-Lys-Tyr-Thr-Thr-NHBn (18) (SEQ ID NO: 1) in good yield (Entry 3). An analogous experiment using the peptide thioacid H-Glu-Tyr-Thr-SH (19) produced H-Glu-Tyr-Thr-Thr-NHBn (20) (Entry 4) (SEQ ID NO: 2). Compatibility of the coupling reaction with aqueous buffer and the denaturant urea was established (Entries 5 & 6). The coupling/ring-opening protocol was also applied to a Cys-containing peptide thioacid 21 to afford a mixture of peptide 22 and its disulfide 23 (Entry 7).[16] Finally, we extended the ligation to the union of thioacids 17 and 19 with the aziridine-containing tripeptide H-Azy(Me)-Phe-Gly-NH$_2$ (24)[17] to give hexapeptides 25 and 26, respectively (Entries 8 & 9). To summarize, the aziridine-mediated ligation is compatible with free NH$_2$, CO$_2$H, OH (aliphatic and aromatic), and SH functional groups (by virtue of in situ protection as a disulfide). The facility of ligation employing an equimolar quantity of relatively hindered thioacid (reaction complete within 1-2 h) is also noteworthy.

The method disclosed herein enables one to synthesize unprotected aziridine-containing peptides and regioselectively hydrolyze the embedded aziridine moiety to give products corresponding to ligation at Xaa-Thr linkages.[18] It is anticipated that the aziridine ring-opening reaction will not be limited to the use of water as a nucleophile.[4,6]

REFERENCES FOR BACKGROUND AND EXAMPLE 1

(1) Reviews: a) Tam, J. P.; Xu, J.; Eom, K. D. *Biopolymers (Peptide Sci.)* 2001, 60, 194-205; b) Nilsson, B. L.; Soellner, M. B.; Raines, R. T. *Annu. Rev. Biophys. Biomol. Struct.* 2005, 34, 91-118; c) Hackenberger, C. P. R.; Schwarzer, D. *Angew. Chem. Int. Ed.* 2008, 47, 10030-10074; d) Kent, S. B. H. *Chem. Soc. Rev.* 2009, 38, 338-351.
(2) Efforts to overcome this requirement include: a) Tam, J. P.; Yu, Q. *Biopolymers* 1998, 46, 319-327; b) Offer, J.; Boddy, C. N. C.; Dawson, P. E. *J. Am. Chem. Soc.* 2002, 124, 4642-4646; c) Wu, B.; Chen, J.; Warren, J. D.; Chen, G.; Hua, Z.; Danishefsky, S. J. *Angew. Chem. Int. Ed.* 2006, 45, 4116-4125; d) Botti, P.; Tchertchian, S. WO/2006/133962; e) Crich, D.; Banerjee, A. *J. Am. Chem. Soc.* 2007, 129, 10064-10065; f) Payne, R. J.; Fichet, S.; Greenberg, W. A.; Wong, C.-H. *Angew. Chem. Int. Ed.* 2008, 47, 4411-4415; g) Okamoto, R.; Kajihara, Y. *Angew. Chem. Int. Ed.* 2008, 47, 5402-5406; h) Haase, C.; Rohde, H.; Seitz, O. *Angew. Chem. Int. Ed.* 2008, 47, 6807-6810; i) Chen, J.; Wan, Q.; Yuan, Y.; Zhu, J.; Danishefsky, S. J. *Angew. Chem. Int. Ed.* 2008, 47, 8521-8524; j) Bennett, C. S.; Dean, S. M.; Payne, R. J.; Ficht, S.; Brik, A.; Wong, C.-H. *J. Am. Chem. Soc.* 2008, 130, 11945-11952; k) Yang, R.; Pasunooti, K. K.; Li, F.; Liu, X.-W.; Liu, C.-F. *J. Am. Chem. Soc.* 2009, 131, 13592-13593; l) Harpaz, Z.; Siman, P.; Kumar, K. S. A.; Brik, A. *ChemBioChem* 2010, 11, 1232-1235; m) Chen, J.; Wang, P; Zhu, J.; Wan, Q.; Danishefsky, S. J. *Tetrahedron* 2010, 66, 2277-2283; n) Shang, S.; Tan, Z.; Dong, S.; Danishefsky, S. J. *J. Am. Chem. Soc.* 2011, 133, 10784-10786.
(3) Danishefsky has reported the HOBt-mediated oxidative coupling of peptide thioacids and free N-terminal peptides. This method is not compatible with unprotected sidechain amines. Wang. P.; Danishefsky, S. J. *J. Am. Chem. Soc.* 2010, 132, 17045-17051.
(4) Okawa, K.; Nakajima, K. *Biopolymers* 1981, 20, 1811-1821.
(5) Korn, A.; Rudolph-Böhner, S.; Moroder, L. *Tetrahedron* 1994, 50, 1717-1730.
(6) Galonic, D. P.; Ide, N. D.; van der Donk, W. A.; Gin, D. Y. *J. Am. Chem. Soc.* 2005, 127, 7359-7369.
(7) Shao, H.; Jiang, X.; Gantzel, P.; Goodman, M. *Chemistry & Biology* 1994, 1, 231-234.
(8) The C2-selective opening of NH aziridine-2-carbonyl-terminated peptides (formed in situ from β-bromoalanylpeptides) by peptide thioacids to give a β-peptide linkage (after S- to N-acyl transfer) was originally observed by Tam et al.: Tam, J. P.; Lu, Y. A.; Liu, C. F.; Shao, J. *Proc. Natl. Acad. Sci. USA* 1995, 92, 12485-12489.
(9) Recently, a convergent synthesis of protected peptidomimetics via the coupling of protected peptide thioacids and protected 2-aziridinylmethylpeptides was reported: Assem, N.; Natarajan, A.; Yudin, A. K. *J. Am. Chem. Soc.* 2010, 132, 10986-10987.
(10) Ag(I) ion is known to promote the oxidative coupling of thioacids and primary amines: a) Schwabacher, A. W.; Bychowski, R. A. *Tetrahedron Lett.* 1992, 33, 21-24; b) Blake, J. *Int. J. Peptide Protein Res.* 1981, 17, 273-274; c) Blake, J.; Li, C. H. *Proc. Natl. Acad. Sci. USA* 1981, 78, 4055-4058.
(11) K$_3$Fe(CN)$_6$, is known to promote the N-acylation of primary amines via dithioacids: Liu, R.; Orgel, L. E. *Nature* 1997, 389, 52-54.
(12) Thioacid 8 was prepared from commercially available Ac-Phe-OH (1. NHS, DCC, DCM, rt, 4 h; 2. NaHS, MeOH, 63% yield) using a known method: Goldstein, A. S.; Gelb, M. H. *Tetrahedron Lett.* 2000, 41, 2797-2800.
(13) The structure of 14 was confirmed through comparison with an authentic sample prepared using standard peptide coupling protocols.
(14) The Fmoc protecting group was retained in this example to facilitate quantitative determination of the epimer ratio.
(15) Peptide thioacids 17, 19, and 21 were prepared by deprotection (TFA, DCM, Et$_3$SiH, 0° C.) of their STmb thioester precursors in 73, 53, and 45% yields.
(16) MS analysis of this coupling reaction indicated predominant formation of a disulfide corresponding to intermediate 12, which implies that the free thiol may be undergoing an in situ protection. Reductive disulfide cleavage likely occurs during the workup with aqueous NaSH, which can act as a reducing agent. Minor products emanating from perthioester intermediates were also detected. See: Liu, C. F.; Rao, C.; Tam, J. P. *Tetrahedron Lett.,* 1996, 37, 933-936.
(17) The aziridine-containing tripeptide 24 was prepared from the union of Tr-Azy(Me)-OH and H-Phe-Gly-NH$_2$ (HATU, DIEA, DMF, rt, 48% yield) followed by deprotection (TFA, (1:1) CHCl$_3$-MeOH, 0° C., 61% yield).
(18) A protocol for ligation at Thr via chemical ligation of a γ-thiol-substituted N-terminal Thr peptide followed by post-ligation desulfurization was recently reported. See reference (2m).

I. Experimental Procedures

Ia. General Considerations. Reagent grade solvents were used for extraction and flash chromatography. All reagents and solvents were purchased from commercial sources and were used without further purification unless otherwise noted. The progress of reactions was monitored by analytical thin layer chromatography (TLC, silica gel F-254 plates) or analytical HPLC (see below). TLC plates were visualized first with UV illumination (254 nm) followed by charring using either ninhydrin stain (0.3% ninhydrin (w/v) in 97:3 EtOH/AcOH) or a modification of Hanessian's stain (10 g ammonium molybdate ((NH$_4$)$_6$Mo$_7$O$_{24}$.4H$_2$O) and 5 g cerium sulfate (Ce(SO$_4$)$_2$) in 1 L 10% aq. H$_2$SO$_4$). Aqueous NaSH was prepared fresh daily by dissolving ~50 mg NaSH hydrate in 1-2 mL of water. Flash column chromatography was performed on flash grade (230-400 mesh) silica gel. The solvent compositions reported for all chromatographic separations are on a volume/volume (v/v) basis. Solvent removal under reduced pressure was performed by rotary evaporation (pressure ~16 mm Hg, bath temperature 25-30° C.) followed by pumping under high vacuum until the container reached a constant mass. High performance liquid chromatography (HPLC) was carried out using an X-Bridge C18 (3×250 mm column) for analytical separations and X-Bridge C18 (19× 150 mm) column for semipreparative purifications. HPLC Eluent B was a solution of 0.1% TFA in MeCN and Eluent A was a 0.1% aqueous TFA solution. HPLC analysis was monitored using dual channel UV detection at 254 and 215 nm. All peptide products purified by preparative HPLC were isolated by removing the MeCN and free TFA by rotary evaporation and the remaining water by lyophilization. Melting points are uncorrected. Optical rotations were recorded at room temperature at the sodium D line (589 nm). $^1$NMR spectra were recorded at ambient temperature, at 300 or 600 MHz, and are reported in parts per million (ppm) on the δ scale relative to tetramethylsilane (δ 0.00). $^{13}$C NMR spectra were recorded at 75.5 or 150.8 MHz and are reported in parts per million (ppm) on the 5 scale relative to CDCl$_3$ (δ 77.00). High resolution mass spectrometry (HRMS) was performed using MALDI in either α-cyano-4-hydroxycinnamic acid or 3,5-dimethoxy-4-hydroxycinnamic acid matrices. Low resolution mass spectrometry (LRMS) was performed using ESI.

Ib. Aziridine and Aziridinyl Peptide Synthesis i. Synthesis of Ac-Azy(Me)-NHBn (7)

H-Azy(Me)-NHBn (6) Tr-Azy(Me)-NHBn$^{1a}$ (S1, 860 mg, 1.99 mmol) was added to an ice-cold stirring solution of 1:1 CHCl$_3$/MeOH (7 mL) and stirred until homogeneous. TFA (3.0 mL, 39 mmol) was added dropwise to the stirring solution over 10 minutes. After 2 h, the reaction was diluted with EtOAc (250 mL) and extracted with water (3×100 mL). The combined aqueous extracts were neutralized by adding portions of sat. NaHCO$_3$ until solution reached pH 8 (litmus). The aqueous solution was extracted with DCM (3×100 mL) and the DCM layers were combined, dried (MgSO$_4$), filtered, and solvent was removed under reduced pressure to afford 6 as clear oil that solidified when stored at 4° C. (360 mg. 95% yield). This solid was used without further purification. R$_f$ 0.24 (6% MeOH/DCM); HPLC: gradient 5% to 70% MeCN/ H$_2$O over 20 min, 0.5 mL/min t$_R$: 12.8 min; $^1$H NMR (300 MHz, CDCl$_3$) δ 7.33-7.23 (5H), 6.92 (bs, 1H), 4.42 (d, J=6.0 Hz, 2H). 2.70 (d, J=6.7 Hz, 1H), 2.38 (m, 1H), 1.29 (bs, 1H), 1.13 (d, J=5.7 Hz, 3H); $^{13}$C NMR (75 MHz, CDCl$_3$) δ 169.4, 138.4, 128.8, 128.0, 127.6, 43.3, 36.6, 32.5, 13.8; HRMS m/z calcd for C$_{11}$H$_{15}$N$_2$O [MH$^+$] 191.1263, found 191.1196.

Ac-Azy(Me)-NHBn (7). A genuine sample of 7 was prepared as follows: To a stirring solution of 6 (46 mg, 0.24 mmol) in DCM (1 mL) was added DIEA (0.200 mL, 1.15 mmol) and Ac$_2$O (0.050 mL, 0.53 mmol). After stirring at rt for 1 h, the reaction mixture was directly loaded onto a silica gel column for chromatographic purification (6% MeOH/ DCM) to afford the desired product as a clear, colorless oil (52 mg, 93% yield). R$_f$ 0.28 (6% MeOH/DCM); HPLC: gradient 5% to 70% MeCN/H$_2$O over 20 min, 0.5 mL/min t$_R$: 14.3 min; $^1$H NMR (300 MHz, CDCl$_3$) δ 7.40-7.14 pH), 6.65 (s, 1H), 4.51 (dd, J=14.7, 6.3 Hz, 1H), 4.36 (dd, J=14.6, 5.6 Hz, 1H), 3.16 (d, J=6.8 Hz, 1H), 2.80-2.70 (m, 1H), 2.10 (s, 3H), 1.25 (d, J=5.7 Hz, 3H); $^{13}$C NMR (75 MHz, CDCl$_3$) δ 182.2, 166.5, 137.9, 129.0, 128.1, 127.9, 43.5, 41.9, 38.6, 23.6, 13.6; HRMS m/z calcd for C$_{13}$H$_{17}$N$_2$O$_2$ [MH$^+$] 233.1290, found 233.1102.

ii. Synthesis of Ac-Phe-Azy(Me)-NHBn (9)

Ac-Phe-Azy(Me)-NHBn (9). A genuine sample of 9 was prepared as follows: Ac-Phe-OH (S2, 50 mg, 0.24 mmol) HOBt (40 mg, 0.30 mmol)+6 (44 mg, 0.23 mmol) were stirred into a suspension in DCM (0.5 mL) at rt. To make the reaction homogenous, a small amount of DMF (~0.3 mL) was added. To the stirring solution was added DIC (50 µL, 0.32 mmol). After 1 h, the resulting white suspension was filtered and the filter cake was washed with EtOAc (10 mL). The filtrate was washed with water (6×10 mL), and the organic layer was dried (MgSO$_4$), filtered, and concentrated by rotary evaporation. Flash chromatographic purification (6% MeOH/DCM) of the crude residue afforded 9 as a white solid (30 mg, 34% yield). R$_f$ 0.18 (6% MeOH/DCM); HPLC: gradient 15% to 50% B in A over 25 min, 0.5 mL/min t$_R$: 22.0 min; $^1$H NMR (300 MHz, CDCl$_3$) δ 7.41-7.01 (10H), 6.34 (bm, J=5.8, 1H), 6.23 (bm, 1H), 4.59 (ddd, J=9.6, 7.1, 5.9, 1H), 4.46 (dd, J=14.7, 6.6, 11-1), 4.27 (dd, J=14.7, 5.5, 1H), 3.09 (dd, J=13.0, 5.8, 1H), 2.98 (dd, J=13.0, 9.6, 1H), 2.89-2.79 (m, 2H), 1.97 (s, 3H), 1.13 (d, J=6.5, 3H); $^{13}$C NMR (75 MHz, CDCl$_3$) δ 183.1, 170.4, 166.3, 138.1, 136.3, 129.5, 128.9, 128.8, 128.1, 127.8, 127.6, 56.6, 43.4, 41.1, 39.1, 38.7, 23.0, 13.4. HRMS m/z calcd for C$_{22}$H$_{26}$N$_3$O$_3$ [MH$^+$] 380.1974, found 380.1980.

iii. Synthesis of H-Azy(Me)-Phe-Gly-NH$_2$ (20)

Fmoc-Phe-Gly-NH$_2$ (S5). To a stirring solution of Fmoc-Phe-OH (S3, 1.800 g, 4.647 mmol)+HATU (1.856 g, 4.881 mmol) in DMF (19.0 mL) was added DIEA (2.40 mL, 13.8 mmol). This solution slowly changed from colorless to yellow over 5 minutes, when the HCl salt of H-Gly-NH$_2$ (S4, 0.444 g, 4.02 mmol) was added and the reaction stirred under dry argon for 3 h. The reaction was subsequently concentrated under high vacuum to ~5 mL, then diluted with EtOAc (500 mL). The resulting yellow solution was sequentially washed with 10% aq. citric acid, sat. NaHCO$_3$, and brine (100 mL each). The organic layer was dried (MgSO$_4$), filtered, and left to stand at rt whereupon S5 began to spontaneously crystalize. After allowing the mixture to stand overnight, a first crop was collected and air-dried (0.949 g, 53% yield, mp 185-187° C.). After successive concentrations and recrystallizations of the mother liquor, subsequent crops had elevated, broader melting ranges (528 mg combined, 28%, mp 195-201° C.). These samples were identical to the first crop by $^1$H NMR analysis. R$_f$ 0.18 (7% MeOH/DCM): $^1$H NMR (300 MHz, DMSO-d$_6$) δ 8.22 (t, J=5.6, 1H), 7.86 (d, J=7.5, 2H), 7.72-7.57 (overlapped d+t, 3H), 7.45-7.06 (13H), 4.24 (ddd, J=10.4, 8.6, 4.1, 1H), 4.19-4.04 (3H), 3.68 (dd, J=17.0, 5.9, 1H), 3.61 (dd, J=17.0, 5.9, 1H), 3.03 (dd, J=13.6, 4.1, 1H), 2.77 (dd, J=13.6, 10.6, 1H); $^{13}$C NMR (75 MHz, DMSO-d$_6$) δ 172.4, 171.4, 156.6, 144.4, 141.3, 138.9, 129.9, 128.7, 128.3, 127.7, 126.9, 126.0, 120.8, 66.4, 56.9, 47.2; HRMS m/z calcd for C$_{26}$H$_{26}$N$_3$O$_4$ [MH$^+$] 444.1923, found 444.1722; m/z calcd for C$_{26}$H$_{25}$N$_3$NaO$_4$ [MNa$^+$] 466.1743, found 466.1622.

Tr-Azy(Me)-Phe-Gly-NH$_2$ (S9). S6 (140 mg, 0.316) was subjected to a standard Fmoc deprotection procedure (see section Ic-ii below) and then and then coupled to Tr-Azy (Me)-OH$^{1b}$ (S8) using the standard HATU coupling procedure (see section Ic-ii). The reaction was diluted with EtOAc (20 mL) and washed sequentially with 10% citric acid (15 mL), water (6×15 mL), and brine (20 mL). The organic layer was dried (MgSO$_4$), filtered, and solvent was removed under reduced pressure. The crude product was purified by flash chromatography (7% MeOH/DCM) to afford S9 as a white foam (83 mg, 48% over two steps). R$_f$ 0.57 (10% MeOH/DCM); HRMS m/z calcd for C$_{34}$H$_{35}$N$_4$O$_3$ [MH$^+$] 547.2709, found 547.2928.

H-Azy(Me)-Phe-Gly-NH$_2$ (24).

Method A: To an ice-cold stirring solution of 1:1 CHCl$_3$/MeOH (1 mL)+S9 (29 mg, 0.053 mmol) was added TFA (3.0 mL, 39 mmol, dropwise over 5 minutes). After 30 minutes, solvent was removed by rotary evaporation (ca. 20 Torr, 22° C.) to afford an oily yellow solid. Et$_2$O (1 mL) was added to the flask to precipitate a slightly sticky white solid. The supernatant was decanted carefully by Pasteur pipette, and the Et$_2$O wash/decant was repeated twice. The white solid had residual solvent removed in vacuo to afford 24 as it is TFA salt (18 mg, 81%). This salt, showing >90% purity by HPLC, was used directly in the subsequent ligation. Analytical samples of the TFA salt of 24 prepared in H$_2$O or MeOH had to be analyzed immediately after being prepared or significant decomposition would be observed.

Method B: The reaction was performed as in method A. The oily yellow solid obtained from rotary evaporation is partitioned between EtOAc (1 mL) and sat. NaHCO$_3$ (3×1 mL). The combined aq. layers were washed with Et$_2$O (2 mL). Residual volatile organics were removed by a brief rotary evaporation. The crude product solution was purified by preparative HPLC to afford 24 as a fluffy white solid (10.1 mg, 61% yield). This lyophilized product was found to be stable to storage in the freezer for 5 days, however when analyzed again after 2 months significant decomposition was observed.

HPLC: gradient 5% to 95% B in A over 25 min, 0.8 mL/min $t_R$: 6.9 min; $^1$H NMR (600 MHz, DMSO-d$_6$) δ 8.71 (d, J=7.9 Hz), 8.30 (t, J=5.7 Hz, 1H), 8.25 (t, J=5.8 Hz), 7.35-7.03 (8H), 4.54 (m, 1H), 3.68 (m, 1H), 3.58 (m, 1H), 3.05 (dd, J=14.0, 4.5 Hz, 1H), 2.84 (dd, J=13.9, 9.9 Hz, 1H), 2.37 (d, J=8.6, 6.8 Hz, 1H), 2.19-2.03 (m, 1H), 1.08 (d, J=5.7 Hz, 1H), 0.53 (d, J=5.5 Hz, 2H); HRMS m/z calcd for C$_{15}$H$_{21}$N$_4$O$_3$ [MH$^+$] 305.1614, found 305.1669; m/z calcd for C$_{15}$H$_{20}$N$_4$NaO$_3$ [MNa$^+$] 327.1433, found 327.1539.

Ic. Thioacid Synthesis i. Synthesis of Ac-Phe-SH (8)

Ac-Phe-OSu (S10). An ice-cold stirring suspension of Ac-Phe-OH (S2, 0.504 g, 2.43 mmol) in DCM (10 mL) was sequentially charged with DCC (0.187 g, 2.95 mmol) and N-Hydroxysuccinimide (NHS, 307 mg, 2.67 mmol). The reaction was stirred for 3.5 h at 0° C., when NMR analysis of the crude reaction mixture showed the reaction to be complete (diagnostic peak for remaining S2 (300 MHz, CDCl$_3$) δ 1.82 ppm). The resulting white suspension was filtered and the filter cake washed with DCM (10 mL). The filtrate was chilled in a −10° C. freezer for 2 h and filtered again with minimal DCM rinsing of the filtercake (1-2 mL). The DCM solution was concentrated by rotary evaporation and the product was precipitated from EtOAc to afford S10 as a white solid (734 mg, 99% yield). This product, contaminated with a negligible amount of dicyclohexylurea, was used without further purification. $^1$H NMR (300 MHz, CDCl$_3$) δ 7.42-7.10 (5H), 5.78 (d, J=7.7 Hz, 1H), 5.29 (m, 1H), 3.33 (dd, J=14.1, 6.1 Hz, 1H), 3.23 (dd, J=14.2, 5.6 Hz, 1H), 2.86 (s, 4H), 1.97 (s, 3H); HRMS m/z calcd for C$_{15}$H$_{16}$N$_2$NaO$_5$ [MNa$^+$] 327.0957, found 327.3312.

Ac-Phe-SH (8). Following the general procedure reported by Gelb,[2] to a stirring solution of S10 (113 mg, 0.371 mmol) in MeOH (3.0 mL) was added with NaSH hydrate (pellet form, 59 mg, 1.0 mmol) at rt. The NaSH dissolved within 5 minutes, resulting in a translucent yellow solution that gradually changed to a yellow opaque suspension during the course of the reaction. After stirring for 2.5 h, the reaction has solvent removed by rotary evaporation and the resulting residue was partitioned between water (5 mL) and EtOAc (2×5 mL). The aq. layer was acidified by dropwise addition of conc. HCl solution (~0.2 mL) to pH 1 (litmus). The acidic layer was extracted with DCM (3×10 mL), and the combined organic extracts were dried (MgSO$_4$), filtered, and solvent was removed under reduced pressure to afford 8 as a colorless oil (52 mg, 63% yield). The product was found to be very unstable to a variety of storage conditions, thus was used immediately in the subsequent ligation reactions. $^1$H NMR (300 MHz, CDCl$_3$) δ 7.46-7.07 (5H), 6.24 (bs, 1H), 4.92 (dt, J=7.5, 5.9, 1H), 3.17 (dd, J=14.2, 5.7, 1H), 3.04 (dd, J=14.3, 7.3, 1H), 1.96 (s, 3H); $^{13}$C NMR (75 MHz, CDCl$_3$) δ 199.1, 170.6, 135.6, 129.5, 129.0, 128.8, 127.6, 61.1, 37.6, 25.7, 23.2.

ii. General Fmoc-Based Solution Phase Peptide Synthesis Protocols.

General Fmoc deprotection procedure of amino acid derivatives: The Fmoc-protected compound was dissolved and stirred in a solution of DCM (0.1 M)+DBU (2 equiv.) at rt. The reaction, unless otherwise noted, was complete within 30 min. The reaction mixture was directly loaded onto a short silica gel column (50 mL dry silica/1 g Fmoc-protected starting material) with minimal DCM rinsing. The column was eluted under pressure (as in flash chromatography, but with the solvent flow rate increased ~300%) with DCM to remove dibenzofulvene and subsequently eluting with 5-10% MeOH in DCM to obtain the free amine. The product had solvent removed under reduced pressure and was used directly in the subsequent coupling step.

General HATU peptide coupling procedure: Reactions were performed using a modified version of Carpino's original procedure:[3] An ice cold stirring solution of the carboxylic acid (1.2 equiv.) In DMF (0.1 M) was sequentially charged with HATU (1.2 equiv.) and DIEA (1.2 equiv.). The resulting solution was stirred for 5 minutes. The free amine (1.0 equiv.) was added as a solution DMF. The ice bath removed after 0.5 h, and the reaction was monitored by TLC for the disappearance of the free amine. Once complete, the reaction was worked up and the product purified as indicated.

iii. Synthesis of Fmoc-Phe-Ala-SH (15).

Fmoc-Phe-Ala-OMe (S13). Fmoc-Phe-OH (S11, 831 mg, 2.15 mmol) HOBt (295 mg, 2.18 mmol) was stirred into an ice-cold suspension in DCM (20 mL). The reaction was charged with DIC (0.340 mL, 2.20 mmol) and stirred for 5 minutes. To the resulting homogenous colorless solution was added the HCl salt of H-Ala-OMe (S12, 251 mg, 1.80 mmol) and DIEA (0.320 mL, 1.84 mmol). After 70 minutes, the resulting suspension was filtered, the filtercake was washed with DCM (10 mL), and the combined filtrates were chilled to −10° C. for 1 h. The mixture was filtered again, then washed with sat. NaHCO$_3$ (2×10 mL) and brine (10 mL). The organic layer was dried (MgSO$_4$), filtered, and concentrated by rotary evaporation. The crude product was precipitated from Et$_2$O and residual solvent was removed under reduced pressure, affording S13 as a white solid (983 mg, 97% yield). The crude product was used without further purification despite a minor contamination of diisopropylurea. An analytical sample was obtained by flash chromatographic purification (35% EtOAc/hexanes). R$_f$ 0.59 (1:1 EtOAc/hexanes); $^1$H NMR (300 MHz, CDCl$_3$) δ 7.77 (d, J=7.5 Hz, 2H), 7.54 (m, 2H), 7.40 (t, J=7.2 Hz, 2H), 7.35-7.15 (7H), 6.29 (d, J=5.6 Hz, 1H), 5.35 (d, J=6.3 Hz, 1H), 4.55-4.41 (overlapped m, 3H), 4.33 (t, J=8.7 Hz, 1H), 4.19 (t, J=6.9 Hz, 1H), 3.71 (s, 3H), 3.14 (dd, J=13.5, 6.2 Hz, 1H), 3.03 (dd, J=13.1, 7.1 Hz, 1H), 1.34 (d, J=7.2 Hz, 1H); HRMS m/z calcd for C$_{28}$H$_{27}$N$_2$O$_5$ [MH$^+$] 473.2067, found 473.1988; m/z calcd for C$_{28}$H$_{26}$N$_2$NaO$_5$ [MNa$^+$] 495.1896, found 495.1872.

Fmoc-Phe-Ala-OSu (S14)+Fmoc-Phe-ala-OSu (epi-S14). To a stirring solution of S13 (483 mg, 1.02 mmol) in 4:1

Me₂CO/H₂O at rt was added 2M aq. NaOH (1.0 mL, 2.0 mmol). After 1 h, TLC analysis indicated the consumption of S13 along with the formation of dibenzolfulvene, indicating partial decomposition of the Fmoc group during this process. Acetone was removed by rotary evaporation, and the aq. layer was washed with $Et_2O$ (5 mL). The aq. layer was carefully acidified to pH 1 with conc. HCl (~0.5 mL), then extracted with DCM (2×20 mL). The DCM extracts were combined, dried ($MgSO_4$), filtered, and had solvent removed under reduced pressure to afford the crude carboxylic acid (231 mg, 49% is yield).[4] The residue was stirred into solution in DCM (10 mL). To the stirring solution was added DCC (170 mg, 0.824 mmol)+NHS (89 mg, 0.77 mmol). With intent to racemize the product at this stage, the reaction was left to stir overnight at rt. The resultant white suspension was filtered, and the filtercake was washed with DCM (10 mL). The combined filtrates were chilled to −10° C. for 1 h. The mixture was filtered again, and solvent was removed by rotary evaporation. Stirring the resulting sticky foam with $Et_2O$/hexanes (1:1, ~4 mL) precipitated a white solid that was significantly easier to handle. Residual solvent was removed under reduced pressure to afford S14 and epi-S14 (285 mg, 49% yield over two steps). As the product is an inseparable mixture, only diagnostic peaks of the $^1H$ NMR are being reported. $^1H$ NMR (300 MHz, $CDCl_3$) δ 7.76 (d, J=7.5 Hz, 1H), 7.53 (dd, J=7.1, 4.3 Hz, 1H), 7.40 (t, J=7.1 Hz, 1H), 2.86 (s), 2.83 (s), 2.82 (s).

Fmoc-Phe-Ala-SH (15)+Fmoc-Phe-Ala-SH (epi-15). The mixture of S14+epi-S14 (102 mg, 0.184 mmol) was dissolved in MeOH (2 mL). To the stirring solution was added NaSH hydrate (29 mg, 0.52 mmol). The reaction changed from a colorless solution to a semi-transparent yellow suspension over the course of 2.5 h. At this time, solvent was removed by rotary evaporation and the residue was partitioned between $H_2O$ (10 mL) and $Et_2O$ (10 mL). After removing trace volatiles by rotary evaporation, a white precipitate formed in the aq. layer. This precipitate was brought back into solution by addition of a small amount of MeOH. The crude product solution was purified by preparative HPLC (in this case, lyophilization required the use of $^tBuOH$ as a co-solvent) to afford 15 (18.4 mg, 21% yield) and epi-15 (3.0 mg, 3% yield). Significant quantities of side-products were observed but were not identified.[4]

15: HPLC: gradient 5% to 100% B in A for 20 min, 0.6 mL/min; $t_R$: 18.0 min; $^1H$ NMR (600 MHz, DMSO-$d_6$) δ 8.54 (bs, 1H), 7.87 (d, J=7.5 Hz, 2H), 7.70 (d, J=8.8 Hz, 1H), 7.67-7.60 (m, 2H), 7.42-7.25 (8H), 7.18 (t, J=7.4 Hz, 1H), 4.37-4.30 (m 1H), 4.27 (ddd, J=11.9, 8.9, 3.4 Hz, 1H), 4.12 (s, 3H), 3.11 (dd, J=13.8, 3.2 Hz, 1H), 2.76 (dd, J=13.8, 11.4 Hz, 1H), 1.30 (d, J=7.1 Hz, 3H); HRMS m/z calcd for $C_{27}H_{26}N_2NaO_4S$ [MNa⁺] 497.1511, found 497.0669.

epi-15: HPLC: gradient 5% to 100% B in A for 20 min, 0.6 mL/min; $t_R$: 17.6 min; HRMS m/z $C_{27}H_{26}N_2NaO_4S$ [MNa⁺] 497.1511, found 497.1478.

iv. Synthesis of H-Lys-Tyr-Thr-SH (17).

Fmoc-Tyr($^tBu$)-Thr($^tBu$)-STmb (S16). S15[5] (469 mg, 0.790 mmol) was subjected to the standard Fmoc deprotection procedure and then coupled to Fmoc-Tyr($^tBu$)-OH using the standard HATU coupling procedure. The reaction was diluted with EtOAc (150 mL), and washed with 10% citric acid solution (50 mL), sat. $NaHCO_3$ (3×50 mL), and brine (50 mL). The organic layer was dried ($MgSO_4$), filtered, and concentrated by rotary evaporation. The crude product was purified by flash chromatography (dry loading the crude product onto silica is strongly recommended; eluted with 40% EtOAc/hexanes) to afford S16 as a white foam (437 mg, 68% yield over two steps).[6] $R_f$ 0.62 (1:1 EtOAc/hexanes); $^1H$ NMR (300 MHz, $CDCl_3$) δ 7.81-6.80 (14H), 6.05 (s, 1H), 5.32 (d, J=8.9, 1H), 4.59-4.41 (m, 2H), 4.27 (m, 2H), 4.16 (m, 2H), 3.75 (bs, 9H), 3.17 (dd, J=13.7, 5.1, 1H), 3.05 (dd, J=14.1, 6.9, 1H), 1.29 (s, 9H), 1.10 (s, 9H); HRMS m/z calcd for $C_{46}H_{56}N_2NaO_9S$ [MNa⁺] 835.3604, found 835.2576.

Fmoc-Lys(Boc)-Tyr($^tBu$)-Thr($^tBu$)-STmb (S17). S16 (420 mg, 0.517 mmol) was subjected to the standard Fmoc deprotection procedure and then coupled to Fmoc-Lys(Boc)-OH using the standard HATU coupling procedure. The reaction was diluted with EtOAc (150 mL), and washed with 10% citric acid solution (50 mL), sat. $NaHCO_3$ (3×50 mL), and brine (50 mL). The organic layer was dried ($MgSO_4$), filtered, and concentrated by rotary evaporation. The crude product was purified using flash chromatography (dry loading the crude product onto silica is strongly recommended, eluted with 1:1 EtOAc/hexanes) to afford S17 as a white foam (413 mg, 77% yield over two steps). $R_f$ 0.29 (1:1 EtOAc/hexanes); $^1H$ NMR (300 MHz, $CDCl_3$) δ 7.81-6.41 (m, 15H), 6.08 (s, 2H), 4.86-4.64 (m, 2H), 4.47 (d, J=8.9, 3H), 4.43-4.14 (m, 6H), 3.79 (s, 3H), 3.77 (s, 6H), 3.20 (dd, J=14.4, 5.9, 1H), 3.02 (m, 3H), 1.83-1.67 (m, 1H), 1.59 (m, 1H), 1.42 (s, 9H), 1.27 (s, 9H), 1.10 (s, 9H); HRMS m/z calcd for $C_{57}H_{76}N_4NaO_{12}S$ [MNa⁺] 1063.5078, found 1063.4727.

H-Lys-Tyr-Thr-SH (17). S17 (48 mg, 0.046 mmol) was subjected to the standard Fmoc de-protection procedure. The amine residue was chilled to 0° C., and the reaction vessel was purged under high vacuum and flushed with argon. An ice-cold solution of TFA (0.600 mL), DCM (0.200 mL), and $Et_3SiH$ (0.250 mL) was charged to the reaction vessel and stirred at 0° C. After 0.5 h, the ice bath was removed and the reaction allowed to warm to ambient to temperature, where it was monitored by HPLC and LRMS until analysis showed the reaction to be complete after an additional 3.5 h. Diagnostic HPLC: isocratic 10% B in A, 2 min, then gradient 10% to 60% B in A over 23 min, 0.6 mL/min; $t_R$: 5.5 min for 17, $t_R$: 17.4 min for H-Lys-Tyr(OH)-Thr(OH)-STmb (identified by LRMS: m/z calcd for $C_{29}H_{43}N_4O_8S$ [MH⁺] 607.1, found 607.1). The reaction was partitioned between water (10 mL) and $Et_2O$ (2×6 mL). The aqueous layer had trace volatiles removed by brief rotary evaporation, and then the crude product solution was purified by preparative HPLC to afford the bis-TFA salt of 17 as a fluffy white solid (22 mg, 73% yield over two steps). HRMS m/z calcd for $C_{19}H_{30}N_4O_5S$ [MH⁺] 427.2015, found 427.2891.

v. Synthesis of H-Glu-Tyr-Thr-SH (19)

Fmoc-Glu($^tBu$)-Tyr($^tBu$)-Thr($^tBu$)-STmb (S18). S16 (285 mg, 0.315 mmol) was subjected to the standard Fmoc deprotection procedure and then coupled to Fmoc-Glu($^tBu$)-OH using the standard HATU coupling procedure. The reaction was diluted with EtOAc (100 mL), and washed with 10% citric acid solution (30 mL), sat. $NaHCO_3$ (2×30 mL), water (20 mL) and brine (30 mL). The organic layer was dried ($MgSO_4$), filtered, and concentrated by rotary evaporation. The crude product was purified using flash chromatography (dry loading the crude product onto silica is strongly recommended, eluted with 45% EtOAc/hexanes) to afford S18 as a white foam that reverted to an clear oil upon standing at rt. Triturating the oil at −78° C. with $Et_2O$/hexanes (~1:10 mixture) and removal of solvent under reduced pressure afforded S18 as a white powder (340 mg, 97% yield over two steps). $R_f$ 0.50 (1:1 EtOAc/hexanes): $^1H$ NMR (300 MHz, $CDCl_3$) δ 7.76 (d, J=7.3, 2H), 7.59 (d, J=7.6, 2H), 7.39 (t, J=7.4, 2H), 7.31 (t, J=7.5, 2H), 7.13 (d, J=8.4, 2H), 6.96 (d, 7.2, 1H), 6.84 (d, J=8.4, 2H), 6.71 (d, J=9.2, 1H), 6.08 (s, 2H), 5.64 (d, J=7.5, 1H), 4.71 (~q, J=7.0, 1H), 4.47 (d, J=8.9, 1H), 4.35 (d, J=6.9, 2H), 4.27 (d, J=7.2, 1H), 4.21 (d, J=6.3, 1H), 4.16 (d, J=2.9, 1H). 3.79 (s, 3H), 3.77 (s, 6H), 3.21 (dd, J=14.2, 5.6, 1H), 3.01 (dd, J=14.1, 7.4, 1H), 2.47-2.20 (2H), 2.11-1.95 (1H), 1.87 (2H), 1.44 (s, 9H), 1.27 (s, 9H), 1.10 (s, 9H).; HRMS m/z calcd for $C_{55}H_{71}N_3NaO_{12}S$ [MNa$^+$] 1020.4656, found 1020.4389.

H-Glu-Tyr-Thr-SH (19). S18 (63.5 mg, 0.0636 mmol) was subjected to the standard Fmoc de-protection procedure. The amine residue was chilled to 0° C., and the reaction vessel was purged under high vacuum and flushed with argon. An ice-cold solution of TFA (0.600 mL), DCM (0.200 mL), and Et$_3$SiH (0.250 mL) was charged to the reaction vessel and stirred at 0° C. After 0.5 h, the ice bath was removed and the reaction was allowed to warm to ambient temperature, where it was monitored by HPLC and LRMS until analysis showed the reaction to be complete after an additional 3.5 h. The reaction was partitioned between water (13 mL) and Et$_2$O (2×6 mL). The aqueous layer had trace volatiles removed by brief rotary evaporation, and then the crude product solution was purified by preparative HPLC to afford the TFA salt of 19 as a fluffy white solid (18.2 mg, 53% yield over two steps). HPLC: isocratic 10% B in A, 2 min, then gradient 10% to 60% B in A over 23 min, 0.6 mL/min; t$_R$: 7.6 min; HRMS m/z calcd for $C_{18}H_{26}N_3O_7S$ [MH$^+$] 428.1491, found 428.1364.

vi. Synthesis of H-Cys-Tyr-Ala-SH (21).

Boc-Ala-STmb (S21). To an ice-cold stirring suspension of S19 (377 mg, 1.99 mmol) S20[7] (427 mg, 1.99 mmol)+HOBt (323 mg, 2.39 mmol) in dry DCM (5 mL, fresh dist. under argon from CaH$_2$) under argon was added DIC (302 mg, 2.39 mmol). The white suspension rapidly changed to a homogenous solution that was allowed to stir overnight and warm to ambient temperature. After 24 h (TLC analysis still showed unreacted S20), the reaction was diluted with DCM (5 mL) and washed with NaHCO$_3$ (2×10 mL), water (2×10 mL), and brine. The organic layer was dried (Na$_2$SO$_4$), filtered, and was concentrated by rotary evaporation. The crude residue was purified by flash chromatography (1:4 EtOAc/hexanes) afforded the desired product S21 (167 mg, 22%) as well as unreacted S20.[4] R$_f$ 0.67 (30% EtOAc/hexanes); $^1$H NMR (300 MHz, CDCl$_3$) δ 6.11 (s, 2H), 5.03 (d, J=7.9, 1H), 4.43 (p, J=7.0, 1H), 4.21 (s, 2H), 3.82 (s, 3H). 3.81 (s, 6H), 1.45 (s, 9H), 1.40 (d, J=7.0, 3H); $^{13}$C NMR (75 MHz, CDCl$_3$) δ 161.1, 159.4, 104.7, 90.7, 56.4, 56.0, 55.6, 28.6, 22.4, 19.6; HRMS m/z calcd for $C_{18}H_{27}NNaO_6S$ [MNa$^+$] 408.1457, found 408.1393.

Fmoc-Tyr($^t$Bu)-Ala-STmb (S22). To a stirring solution of S21 (365 mg, 0.950 mmol) in DCM (6 mL) was added TFA (4 mL). After stirring for 10 minutes, the reaction was washed with a solution of water (10 mL)+20% aq. NaHCO$_3$ (20 mL), then washed once more with 20% aq. NaHCO$_3$ (20 mL). The organic layer was dried (MgSO$_4$), filtered, and had solvent removed under reduced pressure. The free amine residue was used directly in a standard HATU coupling with Fmoc-Tyr($^t$Bu)-OH. The coupling reaction was worked up by diluting with DCM (15 mL) and washing sequentially with sat. NaHCO$_3$ (2×15 mL), water (3×20 mL), and brine (20 mL). The organic layer was dried (MgSO$_4$), filtered, and concentrated by rotary evaporation. Flash chromatographic purification of the crude residue afforded S22 as a white solid (509 mg, 74% yield). R$_f$ 0.82 (5% MeOH/DCM); $^1$H NMR (300 MHz, CDCl$_3$) δ 7.62-6.83 (12H), 6.52 (d, J=6.7, 1H), 6.08 (s, 2H), 5.43 (d, 8.2, 1H), 4.68 (p, J=7.1 Hz, 1H), 4.41 (m 2H), 4.30 (dd, J=10.6, 6.9, 1H), 4.24-4.11 (m, 3H), 3.77 (s, 9H), 3.05 (d, J=5.6, 2H), 1.34 (d, J=7.0, 3H), 1.30 (s, 9H). $^{13}$C NMR (75 MHz, CDCl$_3$) δ 200.7, 170.6, 161.1, 159.4, 154.6, 143.9, 141.5, 130.1, 127.9, 127.3, 125.3, 124.6, 120.2, 90.6, 78.6, 67.3, 56.0, 55.5, 55.1, 47.3, 38.0, 29.0, 22.5, 19.4; HRMS m/z calcd for $C_{41}H_{46}N_2NaO_8S$ [MNa$^+$] 749.2873, found 749.2454.

Boc-Cys(Tr)-Tyr($^t$Bu)-Ala-STmb (S23). S22 (249 mg, 0.34 mmol) was subjected to the standard Fmoc deprotection procedure and then coupled to Boc-Cys(Tr)-OH using the standard HATU coupling procedure. The reaction was diluted with DCM (10 mL), and sequentially washed with sat. NaHCO$_3$ (2×10 mL), water (3×15 mL), and brine (10 mL). The organic layer was dried (MgSO$_4$), filtered, and concentrated by rotary evaporation. The crude residue was purified by flash chromatography (1:1 EtOAc/hexanes) to afford S27 as a white solid (167 mg, 51%). HS-Tmb (S20, 28 mg, 38%) was recovered as a by-product, leading us to conclude that significant decomposition of the thioester occurred during the Fmoc deprotection procedure.[6] R$_f$ 0.28 (30% EtOAc/hexanes); $^1$H NMR (300 MHz, CDCl$_3$) δ 7.52-7.15 (15H), 7.05 (d, J=8.5, 1H), 6.83 (d, J=8.5, 1H), 6.63 (d, J=6.4, 2H), 6.48 (d, 8.1, 2H), 6.09 (s, 2H), 4.69 (d, J=6.7, 1H), 4.58 (p, J=7.3, 2H), 4.19 (d, J=3.7, 2H), 3.79 (s, 3H), 3.77 (s, 6H), 3.02 (dd, J=13.3, 6.1, 1H), 2.55 (dd, J=13.0, 5.2, 1H), 1.38 (s, 9H), 1.31 (s, 9H), 1.25 (d, J=1.8, 3H). $^{13}$C NMR (75 MHz, CDCl$_3$) δ 200.6, 170.3, 170.0, 161.0, 159.3, 154.5, 144.4, 131.1, 130.0, 129.6, 128.2, 127.1, 124.3, 104.5, 90.6, 80.5, 78.4, 67.4, 55.9, 55.4, 55.1, 54.1, 36.8, 33.7, 29.0, 28.3, 22.3, 18.9; HRMS m/z calcd for $C_{53}H_{63}N_3NaO_9S_2$ [MNa$^+$] 972.3903, found 972.3837.

H-Cys-Tyr-Ala-SH (21). Solid S23 (39 mg, 0.041 mmol) placed under argon and chilled to 0° C. In an ice-bath. The solid was dissolved in an ice cold solution of TFA (0.600 mL) DCM (0.150 mL)+Et$_3$SiH (0.250 mL) and stirred into solution. After 6 h, the reaction had reached rt, and HPLC analysis showed the deprotection to be complete. Diagnostic HPLC: isocratic 10% B in A. 2 min, then gradient 10% to 60% B in A over 23 min, 0.6 mL/min; 9.9 min for 21. t$_R$: 20.5 min for H-Cys-Tyr-Ala-STmb (identified by LRMS analysis: m/z calcd for $C_{25}H_{33}N_3NaO_7S_2$ [MNa$^+$] 574.2, found 574.2). It was noted that the HPLC peak belonging to 21 had a small shoulder, and despite our best efforts, better resolution could not be obtained by HPLC. MS analysis of the peak showed no MS peaks other than that assigned to 21. This may be an analytical artifact emanating from its polyfunctional nature or indicate that 21 was partially epimerized during the final global deprotection step ($^1$H NMR of all precursors to 21 show no evidence of an epimer). The reaction was partitioned between water (10 mL) and Et$_2$O (2×6 mL). The aqueous layer had trace volatiles removed by brief rotary evaporation, and then the crude product solution was purified by preparative HPLC to afford the TFA salt of 21 as a fluffy white solid (9 mg, 45% yield). HRMS m/z calcd for $C_{15}H_{22}N_3O_4S_2$ [MH$^+$] 379.1052, found 379.0930: m/z calcd for $C_{15}H_{21}N_3NaO_4S_2$ [MNa$^+$] 394.0871, found 394.0649.

Id. Aziridine+Thioacid Ligations

Preparation of aqueous buffers. Stock solutions of 2.0 M Na$_2$HPO$_4$ in water and 1.0 M citric acid in water were combined in proportions to give phosphate-citrate buffer of the desired pH.[8] The urea-phosphate buffer was prepared by dissolving urea and Na$_2$HPO$_4$ in water, adjusting the pH by adding solid NaOH before bringing the solution up to the desired volume. Using HCl to adjust the pH can lead to undesired decomposition of the aziridine intermediate, thus should be avoided.

i. Reactions to Define Coupling Conditions.

General Procedure for the Metal Mediated Couplings of Thioacetic acid to 6 (Table 3). To a solution of 6 (0.100 mmol) in a 1:1 mixture of DMF and aq. buffer (0.400 mL) was added the appropriate metal salt (1.0 equiv.) and was stirred until homogeneous (in the case of CuCN and CuI, the solution never became homogeneous). To this stirring solution was added AcSH (5, 1.2 equiv.). After 30 minutes, the reaction was filtered through a cotton/celite plug with EtOAc (5 mL) and washed with water (3×5 mL). The organic phase was dried (MgSO$_4$), filtered, and the solvent was removed under reduced pressure. The crude product (85-97% isolated yield) was analyzed by HPLC without further purification. Replicate experiments of entries 1-4, 6, and 10 were performed under argon in degassed solvents. These experiments yielded no significantly different data than obtained from the experiments conducted under the ambient atmosphere.

TABLE 3

Initial Experiments to Define the Coupling Reaction

| Entry | Metal salt | Solvent | 6[a] | 7[a] | Ring-Opening[a] |
|---|---|---|---|---|---|
| 1 | Cu(OAc)$_2$•H$_2$O (100 mol %) | 1:1 DMF-buffer (pH 7.2) | 0% | 100% | 0% |
| 2 | Cu(OAc)$_2$•H$_2$O (100 mol %) | 1:1 DMF-buffer (pH 6.2) | 0% | 100% | 0% |
| 3 | Cu(OAc)$_2$•H$_2$O (100 mol %) | 1:1 DMF-buffer (pH 5.2) | 0% | 100% | 0% |
| 4 | Cu(OAc)$_2$•H$_2$O (100 mol %) | 1:1 DMF-buffer (pH 4.2) | 0% | 100% | 0% |
| 5 | None | 1:1 DMF-buffer (pH 7.2) | 6% | 13% | 81% |
| 6 | AgOAc (100 mol %) | 1:1 DMF-buffer (pH 7.2) | 65% | 35% | 0% |
| 7 | K$_3$Fe(CN)$_6$ (100 mol %) | 1:1 DMF-buffer (pH 7.2) | 0% | 50% | 50% |
| 8 | CuI | 1:1 DMF-buffer (pH 7.2) | 45% | 26% | 29% |
| 9 | CuCN | 1:1 DMF-buffer (pH 7.2) | 55% | 28% | 17% |
| 10 | Cu(OAc)$_2$•H$_2$O (5 mol %) | 1:1 DMF-buffer (pH 7.2) | 26% | 74% | 0% |

[a]Percentages were determined from the HPLC peak integrations of the crude product mixture. Peak identity was determined by LRMS and/or $^1$H NMR analysis.

ii. General Procedures for Table 3.

General Procedure for Ac-Phe-SH (or Ac-phe-SH) H-Azy (Me)-NHBn Ligations (Table 3). To a stirring solution of 6 (0.040 mmol) in the indicated solvent system was Cu(OAc)$_2$.H$_2$O (1.0 equiv.) and, if indicated, HOBt (2.0 equiv.). Once the solution became homogeneous, an aliquot of a 0.4 M stock solution of 8 in DMF (1.1 equiv., final reaction concentration 0.1 M) was added, where it was noted the reaction slowly changed color to a dark brown over the next 5 minutes. Thirty minutes after the addition of 8, the reaction was treated with a dropwise addition of aq. NaSH, which precipitated a black solid. Aq. NaSH addition was halted (usually ~0.3 mL) when it had been determined that no more black solid was forming. The heterogeneous mixture was then filtered through a cotton/Celite plug with EtOAc (5 mL). The organic phase was washed with water (5 mL), dried (MgSO$_4$), filtered, and solvent was removed under reduced pressure to afford a white solid which was analyzed by HPLC and/or $^1$H NMR without further purification.

Identification of epi-9. For identification purposes, mixtures of 8 and ent-8 were prepared by an unoptimized version of the synthesis of 8, starting with Ac-Phe-OH (S2) and Ac-phe-OH (ent-S2), respectively. These mixtures were subjected to an unoptimized version of the general procedure for Ac-Phe-SH H-Azy(Me)-NHBn ligations. For a comparison of ligations using mixtures enriched in 8 vs. mixtures enriched in ent-8 resulting in mixtures of 9 and epi-9, see $^1$H NMR data.

iii. Procedures for Ligation/Ring-Opening Reactions

Ac-Phe-Thr-NHBn (10). To a stirring solution of 6 (0.040 mmol) in DMF (0.300 mL) was added Cu(OAc)$_2$.H$_2$O (1.0 equiv.) and HOBt (2.0 equiv.). Once the solution became is homogeneous and dark green, 8 (0.125 mL, 0.4 M in DMF, 1.2 equiv.) was added. It was noted the reaction slowly changed color over the next 5 minutes. After 30 minutes, the reaction was charged with 10% aq. TFA. After 1.5 h, the reaction was neutralized by adding sat. NaHCO$_3$ and filtered through cotton/Celite with EtOAc (5 mL). The filtrate was washed with sat. NaHCO$_3$ (5 mL), filtered, and solvent was removed by rotary evaporation. The crude product was purified by flash chromatography (10% iPrOH/DCM) to afford 10 (11 mg, 69% yield) as a white solid. R$_f$ 0.14 (10% iPrOH/DCM); $^1$H NMR (300 MHz, CD$_3$OD) δ 7.40-7.09 (10H), 4.67 (dd, J=9.1, 5.9, 1H), 4.37 (s, 21-1), 4.29 (d, J=3.7, 1H), 4.21 (dd, J=6.4, 3.7, 1H), 3.13 (dd, J=17.2, 8.6, 1H), 2.91 (dd, J=13.9, 9.0, 1H), 1.90 (s, 3H), 1.14 (d, 3H); $^1$H NMR (600 MHz, DMSO-d$_6$) δ 8.18 (d, J=8.2 Hz, 1H), 8.08 (t, J=6.1 Hz, 1H), 7.81 (d, J=8.6 Hz, 1H), 7.33-7.17 (9H), 7.15 (t, J=7.1 Hz, 1H), 4.92 (d, J=4.9 Hz, 1H), 4.59 (ddd, J=10.1, 8.4, 4.4 Hz, 1H), 4.28 (overlapped dd, 2H), 4.16 (dd, J=8.6, 3.7 Hz, 1H), 4.05 (complex, overlapped ddt, 1H), 3.01 (dd, J=14.0, 4.3 Hz, 1H), 2.74 (dd, J=14.0, 10.3 Hz, 1H), 1.73 (s, 3H), 1.01 (d, J=6.4 Hz, 3H). $^{13}$C NMR (150.8 MHz, DMSO-d$_6$) δ=172.4, 170.7, 170.0, 162.2, 140.0, 138.8, 129.8, 128.8, 128.7, 127.7, 127.3, 67.0, 59.1, 54.6, 23.1, 20.8; HRMS m/z calcd for C$_{22}$H$_{28}$N$_3$O$_4$ [MH$^+$] 398.2080, found 398.2201; m/z calcd for C$_{22}$H$_{27}$N$_3$NaO$_4$ [MNa$^+$] 420.1899, found 420.2065.

Fmoc-Phe-Ala-Thr-NHBn (16). To a solution of 6 (4.1 mg, 0.022 mmol)+Cu(OAc)$_2$.H$_2$O (4.6, mg, 0.023 mmol) in DMF (0.177 mL) was added HOBt (0.023 mL, 2.00 M in DMF, 0.042 mmol). To the stirring dark green solution was added 15 (10 mg, 0.021 mmol). The reaction color changed to yellow and eventually a very dark brown over the course of 10 minutes. This aziridine intermediate was not detected by analytical HPLC, but was identified by LRMS analysis of the crude reaction mixture (m/z calcd for C$_{38}$H$_{38}$N$_6$NaO$_6$ [MNa$^+$] 653.3, found 653.4). After stirring for 3 h (6 was not detected by LRMS after 1.5 h), the reaction was charged with a solution of TFA (0.060 mL)+H$_2$O (0.500 mL). After 3 h, the reaction was diluted with EtOAc (5 mL) and washed with H$_2$O (3 mL). The organic layer was dried (MgSO$_4$), filtered, and had solvent removed under reduced pressure to afford crude 16 (11.5 mg, 84% yield). HPLC analysis of this crude product determined that the epimerization of this coupling/ring-opening process was 5% (epi-16 was identified by a HPLC co-injection with an authentic sample; see below). The crude product was purified by preparative HPLC (in this case, the HPLC solvent was removed by rotary evaporation, precipitating the product. The product was extracted in DCM and solvent was removed under reduced pressure) to afford 16 as a white solid (9.8 mg, 72% yield) HPLC: gradient 50% to 70% MeCN in H$_2$O over 20 min, 0.6 mL/min; t$_R$: 10.1 min; $^1$H NMR (600 MHz, DMSO-d$_6$) δ 8.37 (d, J=7.1 Hz, 1H), 8.20 (t, 5.7 Hz, 1H), 7.93 (d, J=7.3 Hz, 1H), 7.87 (d, J=7.1 Hz, 2H), 7.68-7.57 (m, 3H), 7.48 (t, J=7.5 Hz, 12H), 7.43-7.14 (m, 414), 4.94 (d, J=5.1 Hz, 1H), 4.43-4.37 (m, 2H), 4.32-4.26 (m 3H), 4.19 (dd, J=8.3, 3.6 Hz, 1H), 4.16-4.08 (m, 3H), 4.05 (dd, J=10.1, 5.3 Hz, 1H), 3.84-3.80 (m, 1H), 3.01 (dd, J=13.8, 2.8 Hz, 1H), 2.76 (dd, J=13.4, 11.4 Hz, 1H), 1.26 (d, J=7.1 Hz, 3H), 1.04 (d, J=6.2 Hz, 3H)$_4$ HRMS m/z calcd for C$_{38}$H$_{40}$N$_4$NaO$_6$ [MNa$^+$] 671.2846, found 671.3943.

Fmoc-Phe-Ala-Thr-NHBn (epi-16). Following the procedure for preparing Fmoc-Phe-Ala-Thr-NHBn, epi-15 (2.6 mg)+6 (1.1 mg) afforded crude epi-16 (3.7 mg, quant.). An aziridine intermediate identical to that above by LRMS was observed. This crude sample was used to identify the epi-16 found in the crude ligation product of 16 (by analytical HPLC co-injection). HPLC analysis of this crude product determined that the epimerization of this coupling/ring-opening process was 5%. The crude product was purified by preparative HPLC (in this case, the HPLC solvent was removed by rotary evaporation, precipitating the product. The product was extracted in DCM and solvent was removed under reduced pressure) to afford epi-16 as a white solid (2.3 mg, 65% yield). HPLC: gradient 50% to 70% MeCN in $H_2O$ over 20 min, 0.6 mL/min; $t_R$: 8.8 min; HRMS m/z calcd for $C_{38}H_{40}N_4NaO_6$ [MNa$^+$] 671.2846, found 671.3868.

H-Lys-Tyr-Thr-Thr-NHBn (18) (SEQ ID NO: 1). 6 (1.9 mg, 0.010 mmol)+Cu(OAc)$_2$·H$_2$O (2.3 mg, 0.012 mmol) HOBt (2.8 mg, 0.021 mmol) were dissolved in DMF (0.200 mL) and stirred at rt until homogeneous and dark green. 17 (bis-TFA salt, 8.0 mg, 0.012 mmol) was added to the reaction mixture, which caused the reaction color to change to yellow and eventually a very dark brown over 10 minutes. HPLC monitoring of the reaction showed complete consumption of 6 in favor of H-Lys-Tyr-Thr-Azy(Me)-NHBn after 2.5 h. Although the aziridine intermediate was not isolated, it was observed by HPLC and LRMS analysis: HPLC: isocratic 10% B in A, 2 min, then gradient 10% to 60% B in A over 23 min, 0.6 mL/min; $t_R$: 14.0 min; LRMS m/z calcd for $C_{30}H_{43}N_6O_6$ [MH$^+$] 583.2, found 583.3; m/z calcd for $C_{30}H_{42}N_6NaO_6$ [MNa$^+$] 605.2, found 605.3. The reaction mixture was charged with a solution of water (0.500 mL) TFA (0.060 mL). After 4 h, the brown heterogeneous mixture was treated with a dropwise addition of aq. NaSH to precipitate a black solid. The reaction was diluted with $H_2O$, and the solid was removed by filtration through a 0.2 μm syringe filter. The filtrate was purified by preparative HPLC to afford 18 as its bis-TFA salt (6.6 mg, 80% yield). HPLC: isocratic 10% B in A, 2 min, then gradient 10% to 60% B in A over 23 min. 0.6 mL/min; $t_R$: 12.3 min; $^1$H NMR (600 MHz, DMSO-d$_6$) δ 9.20 (s, 1H), 8.54 (d, J=7.7, 1H), 8.30 (d, J=8.2, 1H), 8.25 (t, J=5.8, 1H), 8.02 (bs, 3H), 7.67 (bs, 2H), 7.64 (d, J=8.4, 2H), 7.32-7.16 (5H), 7.09 (d, J=7.9, 2H), 6.63 (d, J=7.9, 2H), 5.17 (d, J=4.2, 1H). 4.98 (d, J=3.8, 1H), 4.65 (bs, 1H), 4.35 (dd, J=8.1, 3.5, 1H), 4.28 (d, J=5.8, 1H), 4.22 (dd, J=8.3, 2.5, 1H), 4.08 (d, J=24.3, 2H), 3.70 (bs, 1H), 2.96 (d, J=11.8, 1H), 2.75-2.64 (m, 3H), 1.68 (dd, J=13.5, 6.4, 1H), 1.48 (p, J=7.5, 1H), 1.35-1.23 (m, 2H), 1.05 (d, J=6.2, 3H), 1.01 (d, J=6.0, 3H); HRMS m/z calcd for $C_{30}H_{45}N_6O_7$ [MH$^+$] 601.3350, found 601.3032; m/z calcd for $C_{30}H_{44}N_6NaO_7$ [MNa$^+$] 623.3169, found 623.2794.

H-Glu-Tyr-Thr-Thr-NHBn (SEQ ID NO: 2) (20, General Procedure for Table 2, entries 4-6). 6 (1 equiv.)+Cu(OAc)$_2$·H$_2$O (1 equiv.)+HOBt (2 equiv.) were dissolved in the indicated solvent (0.200 mL) and stirred at rt until dark green (using DMF as a solvent resulted in a homogenous solution, however aq. buffers resulted in line opaque suspensions). 19 (TFA salt, 1 equiv.) was added to the reaction mixture, which caused the reaction color to change to yellow and eventually a very dark brown over 10 minutes. HPLC monitoring of the reaction showed consumption of 6 in favor of H-Glu-Tyr-Thr-Azy(Me)-NHBn within 2 h. Although the aziridine intermediate was not isolated, it was observed by HPLC and LRMS analysis: HPLC: isocratic 10% B in A, 2 min, then gradient 10% to 60% 13 in A over 23 min, 0.6 mL/min; $t_R$: 15.2 min; LRMS m/z calcd for $C_{29}H_{38}N_5O_8$ [MH$^+$] 584.2, found 584.0; m/z calcd for $C_{29}H_{37}N_5NaO_8$ [MNa$^+$] 606.3, found 606.3). The reaction mixture was directly treated with a solution of water (0.500 mL)+TFA (0.060 mL). When HPLC analysis showed the hydrolysis was complete, the brown heterogeneous mixture was treated with a dropwise addition of aq. NaSH to precipitate a black solid. The reaction was diluted with $H_2O$ and the solid was removed by filtration through a 0.2 μm syringe filter. The filtrate was purified by preparative HPLC to afford 20 as its TFA salt (DMF, 69% yield; phosphate-citrate buffer, 71% yield; urea-phosphate buffer, 88% yield). HPLC: isocratic 10% B in A, 2 min, then gradient 10% to 60% B in A over 23 min, 0.6 mL/min; $t_R$: 13.3 min; $^1$H NMR (600 MHz, DMSO-d$_6$) δ 12.27 (s, 1H), 9.18 (s, 1H), 8.53 (d, J=7.9 Hz, 1H), 8.33 (d, J=8.4 Hz, 1H), 8.22 (t, J=6.0 Hz, 2H), 8.02 (d, J=4.3 Hz, 3H), 7.64 (d, J=8.5 Hz, 1H), 7.30-7.15 (5H), 7.10 (d, J=8.5 Hz, 2H), 6.63 (d, J=8.5 Hz, 2H), 5.16 (bs, 1H), 4.95 (bs, 1H), 4.65-4.63 (m, 1H), 4.38 (dd, J=8.4, 4.0 Hz, 1H), 4.28 (d, J=6.2 Hz, 2H), 4.21 (dd, J=8.5, 3.2 Hz, 1H), 4.10 (dd, J=5.7, 3.1 Hz, 1H), 4.06-4.02 (m, 1H), 3.73 (dd, J=10.5, 5.4 Hz, 1H), 2.95 (dd, J=14.0, 3.2 Hz, 1H), 2.65 (dd, J=14.2, 10.6 Hz, 1H), 2.33 (dd, J=8.4, 3.5 Hz, 1H), 2.31 (dd, J=8.1, 3.3 Hz, 1H), 1.92 (dd, J=14.5, 8.0 Hz, 2H), 1.05 (d, J=6.5 Hz, 3H), 1.00 (d, J=6.3 Hz, 3H); HRMS m/z calcd for $C_{29}H_{39}N_5O_9$ [MH$^+$] 602.2826, found 602.2706.

Ligation of H-CYA-SH+H-Azy(Me)-NHBn. 6 (2.5 mg, 0.013 mmol)+Cu(OAc)$_2$·H$_2$O (3.6 mg, 0.018 mmol)+HOBt (4.4 mg, 0.033 mmol) were dissolved in DMF (0.200 mL) and stirred at rt until homogeneous and dark green. 21 (TFA salt, 7.6 mg, 0.016 mmol) was added to the reaction mixture, which caused the reaction color to change to black immediately. HPLC monitoring of the reaction showed incomplete consumption of 6 in favor of the disulfide dimer (H-Cys-Try-Ala-Azy(Me)-NHBn)$_2$ after 2 h. Although the aziridine intermediate was not isolated, it could be observed by HPLC and LRMS: HPLC: isocratic 10% B in A, 2 min, then gradient 10% to 60% B in A over 23 min, 0.6 mL/min; $t_R$: 19.7 min; LRMS m/z calcd for $C_{52}H_{64}N_{10}NaO_{10}S_2$ [MNa$^+$] 1075.4, found 1075.5. It was noted that (I) there was no LRMS evidence for the presence of the H-Cys-Tyr-Ala-Azy(Me)-NHBn and (2) the reaction mixture for this ligation was significantly more complex than the other examples listed in Table 2. The reaction mixture was charged with a solution of water (0.250 mL)+TFA (0.030 mL). After 2.5 h, when the black heterogeneous mixture was treated with a dropwise addition of aq. NaSH to precipitate a black solid. The mixture was diluted with MeOH (7 mL) and the solid was removed by filtration through a 0.2 μm syringe filter. The filtrate was purified by preparative HPLC to afford 22 as its TFA salt (3.5 mg, 40% yield) and 23 as its bis-TFA salt (3.5 mg, 43% yield). Formation of 22 is believed to have been caused by a reduction of the disulfide dimer by the NaSH that was added to precipitate the copper.

22: HPLC: isocratic 10% B in A, 2 min, then gradient 10% to 60% B in A over 23 min, 0.6 mL/min; $t_R$: 14.2 min; HRMS m/z calcd for $C_{26}H_{36}N_5O_6S$ [MH$^+$] 546.2386, found 546.2922; m/z calcd for $C_{26}H_{36}N_5NaO_6S$ [MNa$^+$] 568.2206, found 568.2344.

23: HPLC: isocratic 10% B in A, 2 min, then gradient 10% to 60% B in A over 23 min, 0.6 mL/min; $t_R$: 17.5 min; $^1$H NMR (600 MHz, DMSO-d$_6$) δ 9.20 (s, 1H), 8.72 (bs, 1H), 8.51 (d, J=5.7, 1H), 8.29-8.14 (4H), 7.66 (d, J=8.4, 1H), 7.31-7.23 (6H), 7.20 (t, J=7.1, 2H), 7.05 (d, J=8.2, 1H), 6.63 (d, J=8.4, 2H), 4.94 (bs, 1H), 4.57 (bs, 1H), 4.38 (p, J=7.2 Hz, 1H), 4.32 (dd, J=15.4, 6.2, 1H), 4.26 (dd, J=15.3, 5.8, 1H), 4.23 (dd, J=8.5, 3.6, 1H), 4.03 (s, 2H), 2.96-2.91 (2H), 2.66 (dd, J=13.6, 10.2, 1H), 1.22 (d, J=7.1, 3H), 1.02 (d, J=6.4, 3H). LRMS m/z calcd for $C_{52}H_{67}N_{10}O_{12}S_2$ [MH$^+$] 1089.4, found 1089.4; m/z calcd for $C_{26}H_{36}N_5NaO_6S$ [MNa$^+$] 1089.4, found 1089.4.

Other products: Crude samples of the reaction mixture, both before and after addition of aq. TFA, were analyzed by LRMS, which gave peaks consistent with 21, 22, and 23 (see above). Minor by-products were tentatively identified as follows: observed before addition of aq. TFA: (S24) m/z calcd for $C_{41}H_{50}N_6NaO_9S_2$ [MNa$^+$] 885.3, found 885.4; (S26) m/z calcd for $C_{41}H_{50}N_6NaO_9S_3$ [MNa$^+$] 917.3, found 917.4;

(S27) m/z calcd for $C_{52}H_{64}N_{10}NaO_{10}S_3$ [MNa$^+$] 1114.3, found 1114.2; Observed after aq. TFA addition: (S25) m/z calcd for $C_{41}H_{52}N_8O_{10}S_2$ [MH$^+$] 881.3, found 881.3; (S28) m/z calcd for $C_{52}H_{68}N_{10}O_{12}S_3$ [MH$^+$].

We concluded that these side products emanate from perthioester intermediates. Tam et. al.[9] first disclosed the reaction of thiols and thioacids forming perthiolated products, and the LRMS analysis done on this reaction mixture is consistent with a complex mixture of di-sulfide and tri-sulfide products. An 83% combined yield of the desired products 22 and 23 demonstrates that the aziridine mediated ligation is remarkably faster than the observed side reactions that, presumably, the free thiol causes.

H-Lys-Tyr-Thr-Thr-Phe-Gly-NH$_2$ (25) (SEQ ID NO: 4). 24 (5.0 mg, 0.012 mmol)+Cu(OAc)$_2$.H$_2$O (2.5 mg, 0.013 mmol)+HOBt (3.4 mg, 0.025 mmol) were dissolved in DMF (0.200 mL) and was stirred at rt until homogeneous and dark green. To this solution was added 17, which caused the reaction to change to a dark brown over the next 15 minutes. The formation of H-Lys-Tyr-Thr-Azy(Me)-Phe-Gly-NH$_2$ (SEQ ID NO: 6) was observed by HPLC and LRMS analysis: HPLC: isocratic 10% B in A, 2 minutes, then gradient 10% to 60% B in A over 23 min, 0.6 mL/min; $t_R$: 12.6 min; LRMS m/z calcd for $C_{34}H_{49}N_8O_8$ [MH$^+$] 697.4, found 697.5; m/z calcd for $C_{34}H_{50}N_8NaO_9$ [MNa$^+$] 719.4, found 719.6. When HPLC analysis showed the coupling to be complete (2 h), the reaction mixture was charged with a solution of TFA (0.060 mL)+H$_2$O (0.500 mL). After 3.5 h, the reaction mixture was treated with aq. NaSH to precipitate a black solid. The solid was removed by flushing the reaction mixture through a 0.2 μm syringe filter with MeOH (10 mL). The filtrate had solvent removed by rotary evaporation and was reconstituted in water for purification by preparative HPLC to afford the TFA salt of 25 as a white solid (8.8 mg, 78% yield). HPLC: isocratic 10% B in A, 2 min, then gradient 10% to 60% B in A for 23 min, 0.6 mL/min; $t_R$: 11.1 min; $^1$H NMR (600 MHz, DMSO-d$_6$) δ 9.20 (s, 1H), 8.53 (d, J 8.1, 1H), 8.26 (d, J=8.4, 1H), 8.19 (t, J=5.8, 1H), 8.01 (d, J=7.5, 4H), 7.65 (s, 3H), 7.58 (d, J=8.1, 2H), 7.26-7.03 (m, 9H), 6.63 (d, J=8.5, 2H), 5.07 (d, J=4.5, 1H), 4.97 (d, J=5.0, 1H), 4.69-4.61 (m, 1H), 4.49 (td, J=8.4, 5.3, 1H), 4.32 (dd, J=8.4, 3.8, 1H), 4.21 (dd, J=8.1, 3.9, 1H), 4.03 (qd, J=10.5, 5.5, 2H), 3.70 (bs, 1H), 3.64 (dd, J=16.8, 6.1, 1H), 3.55 (dd, J=16.8, 5.6, 1H), 3.04 (dd, 14.0, 5.1, 1H), 2.97 (dd, J=14.2, 3.5, 1H), 2.81 (dd, J=13.9, 6.8, 1H), 2.71 (bs, 2H), 2.67 (dd, J=14.5, 10.5, 1H), 1.68 (dd, J=14.4, 7.1, 2H), 1.48 (p, J=7.5, 2H), 1.35-1.22 (m, 2H), 1.00 (d, J=6.3, 3H), 0.99 (d, J=6.3, 3H); HRMS m/z calcd for $C_{34}H_{51}N_8O_9S$ [MH$^+$] 715.3779, found 715.3059.

H-Glu-Tyr-Thr-Thr-Phe-Gly-NH$_2$ (26) (SEQ ID NO: 5). 24 (5.6 mg, 0.018 mmol) Cu(OAc)$_2$ (0.019 mmol from an aq. stock solution) HOBt (0.038 mmol from a 2.00M DMF stock solution) were dissolved in buffer (0.105 mL, 8M Urea, 0.1 M Pi, pH 7.53), and was stirred at rt until homogeneous and dark green. To this solution was added 19 (9.9 mg, 0.018 mmol), which caused the reaction to change to a dark brown immediately. The formation of H-Glu-Tyr-Thr-Azy(Me)-Phe-Gly-NH$_2$ (SEQ ID NO: 7) was observed by HPLC and LRMS analysis: HPLC: isocratic 10% B in A, 2 minutes, then gradient 10% to 60% B in A over 23 min, 0.6 mL/min; $t_R$: 13.0 min; LRMS m/z calcd for $C_{33}H_{44}N_7O_{10}$ [MH$^+$] 698.1, found 698.2; m/z calcd for $C_{33}H_{43}N_7NaO_{10}$ [MNa$^+$] 720.4, found 720.4. When HPLC analysis showed the coupling to be complete (2 h), the reaction mixture was charged with a solution of TFA (0.060 mL)+H$_2$O (0.500 mL). After 2 h, the reaction mixture was treated with aq. NaSH to precipitate a black solid. The solid was removed by flushing the reaction mixture through a 0.2 μm syringe filter with MeOH (10 mL). The filtrate had solvent removed by rotary evaporation and was reconstituted in water for purification by preparative HPLC to afford the TFA salt of 26 as a white solid (11.4 mg, 77% yield). HPLC: isocratic 10% B in A, 2 min, then gradient 10% to 60% B in A over 23 min, 0.6 mL/min; $t_R$: 11.3 min; $^1$H NMR (600 MHz, DMSO-d$_6$) δ 9.18 (s, 1H), 8.52 (d, J=7.9 Hz, 1H), 8.29 (d, J=8.5 Hz, 1H), 8.17 (t, J=5.9 Hz, 1H), 8.02-8.00 (m, 4H), 7.61 (d, J=8.1 Hz, 1H), 7.27-7.03 (m, 9H), 6.63 (d, J=8.5 Hz, 2H), 5.06 (s, 1H), 4.93 (s, 1H), 4.68-4.60 (m, 1H), 4.47 (td, J=8.1, 5.4 Hz, 1H), 4.34 (dd, J=8.4, 3.9 Hz, 1H), 4.20 (dd, J=8.1, 3.9 Hz, 1H), 4.06-3.95 (m, 2H), 3.73 (bd, J=5.2 Hz, 1H), 3.63 (dd, J=16.7, 6.0 Hz, 1H), 3.54 (dd, J=16.8, 5.6 Hz, 1H), 3.03 (dd, J=14.1, 5.1 Hz, 1H), 2.95 (dd, J=14.2, 3.2 Hz, 1H), 2.81 (dd, J=13.9, 8.8 Hz, 1H), 2.65 (dd, J=14.2, 10.5 Hz, 1H), 2.34-2.29 (m, 2H), 1.91 (dd, J=14.7, 7.9 Hz, 2H), 0.99 (overlapped d, 6H); HRMS m/z calcd for $C_{33}H_{46}N_7O_{11}$ [MH$^+$] 716.3255, found 716.3186; m/z calcd for $C_{33}H_{45}N_7NaO_{11}$ [MN$^+$] 738.3075, found 738.2970.

Ie. Synthesis of a Genuine Sample of 14.

Fmoc-Thr($^t$Bu)-NHBn (S30). Benzylamine (0.270 g, 2.52 mmol) was coupled to Fmoc-Thr($^t$Bu)-OH (S29, 1.00 g, 2.52 mmol) using the standard HATU coupling procedure. The reaction was diluted with Et$_2$O (150 mL), and washed with 10% citric acid solution (60 mL), water (3×60 mL), and brine (60 mL). The organic layer was dried (MgSO$_4$), filtered, and concentrated by rotary evaporation. The crude product was purified using flash chromatography (15% EtOAc/hexanes) to afford S30 as a white solid (1.20 g, 98% yield). R$_f$ 0.53 (1:1 EtOAc/hexanes); $^1$H NMR (300 MHz, CDCl$_3$) δ 7.77 (d, J=7.5 Hz, 2H), 7.61 (d, J=7.4 Hz, 2H), 7.44-7.27 (m, 9H), 6.06 (d, J=4.6 Hz, 2H), 4.50 (dd, J=7.8, 5.7 Hz, 2H), 4.44-4.37 (m, 2H), 4.27-4.14 (m, 3H), 1.24 (s, 9H), 1.04 (d, J=6.5 Hz, 3H); HRMS m/z calcd for $C_{30}H_{34}N_2NaO_4$ [MNa$^+$] 509.2416, found 509.2226.

Fmoc-Phe-Thr($^t$Bu)-NHBn (S31). S30 (0.300 g, 0.617 mmol) was subjected to the standard Fmoc deprotection procedure and then coupled to Fmoc-Phe-01-1 (0.263 g, 0.678 mmol) using the standard HATU coupling procedure. The reaction was diluted with Et$_2$O (90 mL), and washed with 10% citric acid solution (40 mL), water (3×60 mL), and brine (60 mL). The organic layer was dried (MgSO$_4$), filtered, and concentrated by rotary evaporation. The crude product was purified using flash chromatography (30% EtOAc/hexanes) to afford S31 as a white solid (0.344 g, 88% yield over two steps). R$_f$ 0.33 (1:1 EtOAc/hexanes); $^1$H NMR (300 MHz, CDCl$_3$) δ 7.77 (d, J=7.6 Hz, 2H), 7.53 (dd, J=7.1, 5.2 Hz, 2H), 7.40 (t, J=7.5 Hz, 2H), 7.34-7.10 (14H), 5.30 (d, J=6.2 Hz, 1H), 4.55-4.34 (m, 4H), 4.30-4.08 (m, 4H), 3.11 (d, J=6.4 Hz, 2H), 1.18 (s, 9H), 0.94 (d, J=6.1 Hz, 3H); HRMS m/z calcd for $C_{39}H_{43}N_3NaO_5$ [MNa$^+$] 656.3100, found 656.2769.

Ac-Phe-Thr($^t$Bu)-NHBn (S32). S31 (0.186 g, 0.293 mmol) was subjected to the standard Fmoc deprotection procedure. The resulting residue was dissolved in a solution of DCM (2 mL), Ac$_2$O (0.060 g, 0.587 mmol), and DIEA (0.076 g, 0.587 mmol) and stirred for 30 minutes at rt. The reaction was diluted with EtOAc (60 mL), washed with water (20 mL), and brine (20 mL). The organic layer was dried (MgSO$_4$), filtered, and concentrated by rotary evaporation. The crude product was purified using flash chromatography (5% MeOH/DCM) to afford S32 as a white solid (0.115 g, 95% yield over two steps). R$_f$ 0.36 (5% MeOH/DCM); $^1$H NMR (300 MHz, CDCl$_3$) δ 7.34-7.13 (10H), 6.88 (d, J=5.8 Hz, 1H), 6.15 (d, J=7.3 Hz, 1H), 4.72 (q, J=6.8 Hz, 1H), 4.51-4.33 (m, 3H), 4.25-4.14 (m, 2H), 3.08 (dd, J=6.7, 4.2 Hz, 2H), 1.97 (s, 3H), 1.16 (s, 9H), 0.96 (d, J=6.3 Hz, 3H); HRMS m/z calcd for $C_{26}H_{36}N_3O_4$ [MH$^+$] 454.2706, found 454.2490; m/z calcd for $C_{26}H_{35}N_3NaO_4$ [MNa$^+$] 476.2525, found 476.2502.

Ac-Phe-Thr-NHBn (14). S32 (0.070 g, 0.154 mmol) was dissolved in an ice cold solution of TFA (0.600 mL) DCM (0.150 mL) Et$_3$SiH (0.250 mL) and stirred for 0.5 h. The ice bath was removed and the reaction was allowed to stir at rt for an additional 2 hours. The reaction was diluted with EtOAc (40 mL), and washed with sat. NaHCO$_3$ (2×25 mL), water (25 mL), and brine (25 mL). The organic layer was dried (MgSO$_4$), filtered, and concentrated by rotary evaporation to afford 14 as a white solid (0.050 g, 82% yield). R$_f$ 0.14 (10% iPrOH/DCM); $^1$H NMR (300 MHz, CD$_3$OD) δ 7.33-7.15 (10H), 4.68 (dd, J=9.0, 5.9 Hz, 1H), 4.36 (s, 2H), 4.30 (d, J=3.7 Hz, 1H), 4.21 (dd, J=6.4, 3.7 Hz, 1H), 3.14 (dd, J=13.9, 5.9 Hz, 1H), 2.91 (dd, J=13.9, 9.0 Hz, 1H), 1.89 (s, 3H), 1.14 (d, J=6.4 Hz, 3H). The spectra obtained from this experiment overlaps perfectly with that of 14 prepared from the ligation/ring-opening procedure.

REFERENCE AND NOTES FOR EXPERIMENTAL PROCEDURES (1) a) The experimental procedures for synthesizing 6 and the preparation of trityl aziridine precursor Tr-Azy(Me)-NHBn (S1) from Thr were previously reported by Gin et. al. (see below), however 6 was not isolated and no spectroscopic data reported. b) The synthesis of Tr-Azy(Me)-OH from Tr-Azy(Me)-OBn was performed as reported. See Galonic, D. P.; Ide, N. D.; van der Donk, W. A.; Gin, D. J. Am. Chem. Soc. 2005, 127, 7359-7369 (and references therein).
(2) Goldstein, A. S.; Gelb, M. H. Tetrahedron Lett. 2000, 41, 2797-2800.
(3) Carpino, L. A. J. Am. Chem. Soc. 1993, 115, 4397-4398
(4) There were no efforts made to optimize this experimental procedure.
(5) Barlett, K. N.; Kolakowski, R. V.; Katukojvala, S.; Williams, L. J. Org. Lett. 2006, 8, 823-826
(6) Thioesters are known to be labile during Fmoc-deprotection, thus the low yields on these reactions are not surprising. For a discussion on thioester reactivity in the context of solid phase peptide synthesis, see Crich, D.; Sana, K. J. Org. Chem. 2009, 74, 7383-7388 (and references therein).
(7) Vetter, S. Synth. Commun. 1998, 28, 3219-3273.
(8) McIlvaine, T. C. J. Biol. Chem. 1921, 49, 183-186
(9) Liu, C. F.; Rao, C.; Tam, J. P. Tetrahedron Lett. 1996, 37, 933-936.

Example 2

Glycosylation Ligation Products and Procedures

The coupling of Ac$_3$GlcNAcβ-NH$_2$ (A4) and Cbz-Gly-SH (A5) to provide the readily isolated product A6 (Table 4), confirming that the aziridine-mediated ligation conditions did, indeed, result in the desired amide bond formation (Entry 1). Reaction optimization studies (Entries 2-6) indicated that the maximum yield of A6 was obtained when the thioacid was added to the Cu(II)-HOBt complex followed by a four-fold excess of glycosylamine (entry 5). These conditions minimized the detrimental effect resulting from the known propensity of glycosylamines towards hydrolysis. Only marginal improvement in yield accompanied further increase in the amount of A6 used. This reaction was complete after 30 minutes at room temperature. Control experiments demonstrated the necessity for both Cu(II) and HOBt in the reaction (Entries 7 and 8). A known oxidative protocol[9] did not produce 6 after 30 minutes (Entry 9). The desired reaction could be "rescued" by the inclusion of Cu(OAc), but DMSO was deemed to be inferior to DMF (Entry 10).

TABLE 4

Reaction Optimization and Control Experiments

| Entry | Equiv of A4 | Equiv of A5 | Reaction Conditions | Yield of A6 |
|---|---|---|---|---|
| 1 | 1.0 | 1.0 | Cu(OAc)$_2$ (1.0), HOBt (2.0) aq. DMF$^a$ | 64%$^c$ |
| 2 | 1.0 | 1.0 | Cu(OAc)$_2$ (1.0), HOBt (2.0), aq. DMF$^b$ | 68%$^d$ |
| 3 | 2.0 | 1.0 | Cu(OAc)$_2$ (1.0), HOBt (2.0), aq. DMF$^b$ | 75%$^d$ |
| 4 | 3.0 | 1.0 | Cu(OAc)$_2$ (1.0), HOBt (2.0), aq. DMF$^b$ | 81%$^d$ |
| 5 | 4.0 | 1.0 | Cu(OAc), (1.0), HOBt (2.0), aq. DMF$^b$ | 90%$^c$ |
| 6 | 5.0 | 1.0 | Cu(OAc), (1.0), HOBt (2.0), aq. DMF$^b$ | 92%$^d$ |
| 7 | 1.0 | 1.1 | HOBt (2.2), DMF$^b$ | 0%$^e$ |
| 8 | 1.0 | 1.1 | Cu(OAc)2 (1.0), aq. DMF$^b$ | 0%$^c$ |
| 9 | 4.0 | 1.0 | HOBt (2.0), DMSO | 0%$^d$ |
| 10 | 4.0 | 1.0 | Cu(OAc)2 (1.0), HOBt (2.0), aq. DMSO$^b$ | 83%$^d$ |

$^a$Order of addition: aq Cu(OAc)$_2$•H$_2$O, HOBt, amine, thioacid.
$^b$Order of addition: aq Cu(OAc)$_2$•H$_2$O thioacid, amine.
$^c$Isolated yield.
$^d$Quantitative HPLC analysis
$^e$TLC analysis.

With an optimized glycosylation protocol in hand, we next examined the chemoselectivity issue employing our optimized reaction conditions and substrates that did not incorporate protecting groups (Table 5). The coupling of GlcNAcβ-NH$_2$ (A7) and to thioacid A5 gave glycosylated amino acid A8 in 94% isolated yield (Entry 1), demonstrating the feasibility of using unprotected glycosylamines in the reaction. The coupling of peracetylated glycosylamine A4 and the unprotected tripeptide thioacid H-Leu-Asn-Phe-SH (A9) provided our first test of peptide amine chemoselectivity, cleanly producing A10 in 72% isolated yield (Entry 2). Careful HPLC-MS analysis of the reaction mixture showed no evidence of interference by the N-terminal amine, confirming the chemoselectivity. Building on these two experiments, the coupling of unprotected glycosylamine A7 and unprotected thioacid A9 afforded the product A11 in 81% isolated yield (Entry 3).

Moving on to examples that are directly related to glycobiology, we next examined the glycosylative ligation in the context of aspartylation using the heptapeptide thioacid A12

SEQ ID NO: 8), a compound that contains unprotected amine and alcohol moieties. The coupling of A4 and A12 proceeded smoothly in the presence of both the N-terminal amine and unprotected Lys sidechain to afford the glycopeptide A13 (SEQ ID NO: 9) in 55% isolated yield (Entry 4). As expected, the ligation of A7 and A12 gave the glycopeptide A14 (SEQ ID NO: 10) in 65% isolated yield (Entry 5). Finally, the reaction of chitobiosylamine (A15) and thioacid A12 produced the glycopeptide A16 (SEQ ID NO: 11) in 53% isolated yield (Entry 6). This example demonstrated the compatibility of glycosylative ligation with an intersaccharide acetal linkage. None of the aspartimide that often accompanies N-glycosylation procedures was observed in these ligation reactions. The point of glycan attachment to peptide in A16 (co-aspartylation) was confirmed by means of a ROESY NMR experiment. In each case, the mass balance was accounted for by isolation of the thioacid hydrolysis byproduct. Products A14 and A16 correspond to truncated segments of the common α subunit found in human glycoprotein hormones (e.g. human chorionic gonadotropin, hCG).

TABLE 5

Chemoselective N-Glycosylation Reactions[a]

| Entry | Glycosylamine | Thioacid |
|---|---|---|
| 1 | 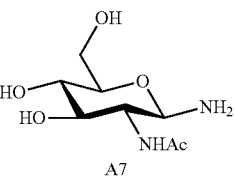<br>A7 | 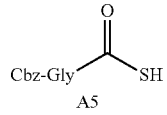<br>Cbz-Gly, A5 |
| 2 | 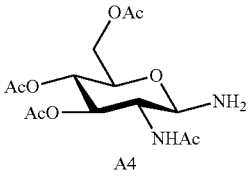<br>A4 | 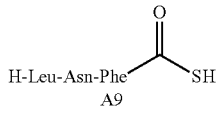<br>H-Leu-Asn-Phe, A9 |
| 3 | 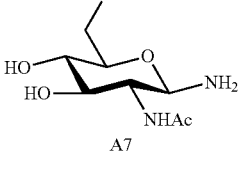<br>A7 | 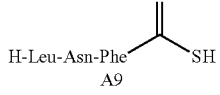<br>H-Leu-Asn-Phe, A9 |
| 4 | 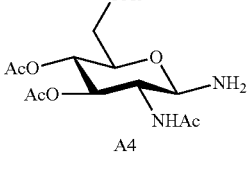<br>A4 | 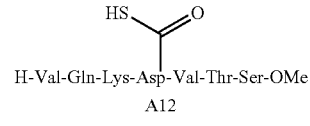<br>H-Val-Gln-Lys-Asp-Val-Thr-Ser-OMe, A12 |
| 5 | 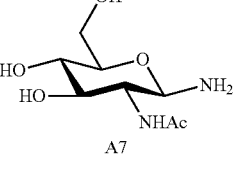<br>A7 | 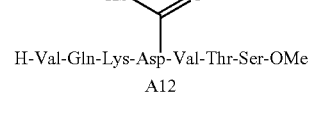<br>H-Val-Gln-Lys-Asp-Val-Thr-Ser-OMe, A12 |
| 6 | 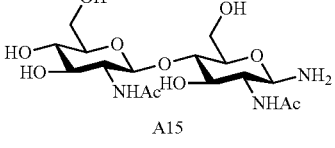<br>A15 | 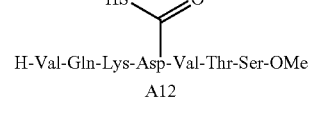<br>H-Val-Gln-Lys-Asp-Val-Thr-Ser-OMe, A12 |

TABLE 5-continued

Chemoselective N-Glycosylation Reactions[a]

| Entry | Ligation Product | Yield |
|---|---|---|
| 1 | 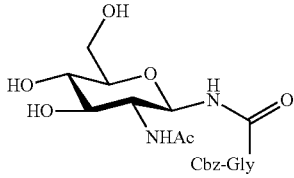<br>A8 (Cbz-Gly) | 94% |
| 2 | 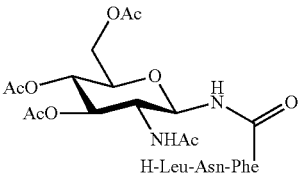<br>A10 (H-Leu-Asn-Phe) | 72%[b] |
| 3 | 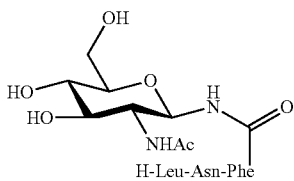<br>A11 (H-Leu-Asn-Phe) | 81%[c] |
| 4 | 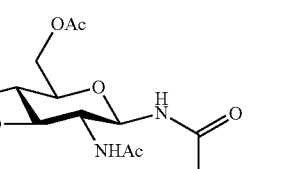<br>A13 (H-Val-Gln-Lys-Asn-Val-Thr-Ser-OMe) | 55%[d] |
| 5 | 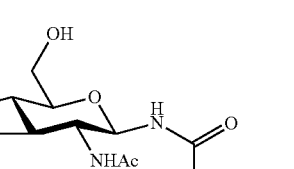<br>A14 (H-Val-Gln-Lys-Asn-Val-Thr-Ser-OMe) | 65%[e] |
| 6 | 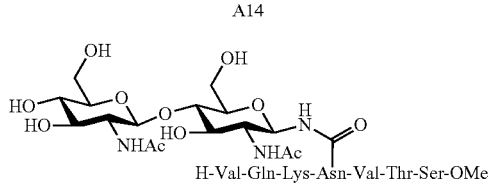<br>A18 (H-Val-Gln-Lys-Asn-Val-Thr-Ser-OMe) | 53%[f] |

[a] The optimized conditions from TABLE 1, Entry 5 were used for these reactions.
[b] 19% of hydrolysed thioacid was isolated.
[c] 5% of hydrolyzed thioacid was isolated.
[d] 32% of hydrolyzed thioacid was isolated.
[e] 21% of hydrolyzed thioacid was isolated.
[f] 30% of hydrolyzed thioacid was isolated.

Synthesis of GlcNAcβ-NH$_2$ (A7).[1]

GlcNAcβ-N3 (SB2). A flame dried flask was charged with finely chopped Mg ribbon (0.150 g, 6.17 mmol) followed by MeOH (7.4 mL, freshly dist. from CaH$_2$). The suspension was stirred under argon until the reaction was homogeneous, at which point a solution of SB1 (0.250 g, 0.672 mmol) in MeOH (7.4 mL, freshly dist. from CaH$_2$) was added via syringe under argon. After three hours, the solution was quenched by the addition of water (10 mL) followed by Amberlyst 15 ion exchange resin (4 g). The suspension was stirred vigorously for 10 minutes, filtered, and the filtrate was concentrated in vacuo to give S2 as a white solid (0.140 g, 94% yield) which was used without further purification. R$_f$ 0.72 (50% MeOH/CHCl$_3$). mp 140-145° C. (lit. 142° C.

dec.).[2b] $^1$H NMR (400 MHz, D$_2$O) δ 4.61 (d, J=9.2 Hz, 1H), 3.78 (dd, J=12.5, 2.1 Hz, 1H), 3.62 (dd, J=12.4, 5.4 Hz, 1H), 3.56 (app. t, J=10.1, 9.3 Hz, 1H), 3.43 (app. t, J=10.2, 8.6 Hz, 1H), 3.42-3.37 (m, 1H), 3.33 (app. t, J=9.7, 8.7 Hz, 1H), 1.91 (s, 3H).

GlcNAcβ-NH$_2$ (A7). GlcNAcβ-N$_3$(SB2) (0.130 g, 0.587 mmol) was added to a suspension of 10% w/w Pd/C (0.062 g, 0.059 mmol) in MeOH. The suspension was purged and placed under an H$_2$ atmosphere, stirred for 2 hours, and then filtered through a pad of Celite. The filter pad was rinsed with MeOH (75 mL), and the combined filtrates were concentrated in vacua to give A7 as a white solid (0.125 g, 95% yield). R$_f$ 0.20 (50% MeOH/CHCl$_3$). mp 95-115° C. dec., (lit. 103-112° C. dec.),[1] $^1$H NMR (400 MHz, D$_2$O) δ 4.01 (d, J=9.1 Hz, 1H), 3.76 (d, J=12.2 Hz, 1H), 3.60-3.55 (m, 1H), 3.48 (t, J=9.6 Hz, 1H), 3.42-3.35 (m, 2H), 3.29 (d, J=5.1 Hz, 2H), 3.21 (s, 2H), 1.91 (s, 3H).

Synthesis of H-Leu-Asn-Phe-SH (A9).

Boc-Asn-Phe-SFm (SB4). SB3 (1.20 g, 2.61 mmol) was subjected to the general Boc deprotection procedure (solution phase) and then coupled to Boc-Asn-OH (0.664 g, 2.86 mmol) using the standard HATU coupling procedure (solution phase). After 1 h the coupling reaction was worked up by diluting with EtOAc (60 mL) and washing sequentially with 10% citric acid solution (2×30 mL), sat. NaHCO$_3$ (2×30 mL), water (2×30 mL), and brine (30 mL). The organic layer was dried (MgSO$_4$), filtered, and solvent removed in vacua. The crude product was purified by flash chromatography using a 3% MeOH/DCM eluent and dry loading the sample to give S4 as a white solid (1.34 g, 90% yield over two steps). R$_f$ 0.34 (5% MeOH/DCM). mp 178-195° C. dec. $^1$H NMR (300 MHz, CDCl$_3$) δ 7.75 (d, J=8.1 Hz, 2H), 7.60-7.54 (m, 2H), 7.40 (t, J=7.4 Hz, 3H), 7.35-7.28 (m, 3H), 7.05-7.00 (m, 2H), 6.57 (d, J=8.2 Hz, 1H), 5.00 (br d, J=8.8 Hz, 1H), 4.82 (ddd, J=8.3, 7.2, 5.8 Hz, 1H), 4.35 (app. q, J=7.1 Hz, 1H), 4.16 (t, J=5.7 Hz, 1H), 3.59 (dd, J=11.7, 5.6 Hz, 1H), 3.53 (dd, J=11.9, 5.8 Hz, 1H), 3.03 (dd, J=14.1, 5.8 Hz, 1H), 2.89 (dd, J=14.2, 7.2 Hz, 1H), 2.82-2.66 (m, 2H), 1.44 (s, 9H). $^{13}$C NMR (100 MHz, DMSO-d$_6$) δ 200.1, 169.8, 155.6, 145.5, 145.4, 141.1, 141.1, 137.1, 129.4, 128.7, 128.1, 127.6, 127.5, 127.0, 125.1, 125.1, 120.4, 118.3, 79.1, 61.1, 50.6, 46.1, 36.9, 31.5, 28.5, 20.6. HRMS m/z calcd for C$_{32}$H$_{35}$N$_3$O$_5$S [MH$^+$] 596.2297, found 596.3236.

Fmoc-Leu-Asn-Phe-SFm (SB5). SB4 (0.971 g, 1.69 mmol) was subjected to the general Boc deprotection procedure (solution phase) and then coupled to Fmoc-Leu-OH (0.528 g, 1.49 mmol) using the standard HATU coupling procedure (solution phase). After 2 h, the reaction was worked up by diluting with EtOAc (150 mL) and washing sequentially with 10% citric acid solution (2×30 mL), sat. NaHCO$_3$ (2×30 mL), water (2×30 mL), and brine (30 mL). During the workup procedure, the product began to precipitate in the organic layer, which was subsequently concentrated by rotary evaporation. The resultant yellow solid was rinsed via vacuum filtration sequentially with Et$_2$O (10 mL), MeOH (10 mL), and DCM (10 mL). The residue was dried in vacuo to give S5 as a white solid (0.981 g, 81% yield over two steps). R$_f$ 0.31 (5% MeOH/DCM), mp 195-208° C. $^1$H NMR (400 MHz, DMSO-d$_6$) δ 8.50 (d, J=7.5 Hz, 1H). 8.06 (d, J=7.8 Hz, 1H), 7.84 (t, J=9.1, 8.3 Hz, 1H), 7.67 (dd, J=12.2, 7.5 Hz, 2H), 7.60 (dd, J=11.0, 7.5 Hz, 2H), 7.47 (d, J=8.3 Hz, 1H), 7.40-7.33 (m, 4H). 7.32-7.24 (m, 5H), 7.21-7.05 (m, 6H), 6.89 (s, 1H), 4.51 (td, J=8.1, 5.0 Hz, 1H), 4.40-4.21 (m, 2H), 4.17 (m, 3H), 3.98 (td, J=10.1, 4.7 Hz, 1H), 3.45 (d, J=6.9 Hz, 2H), 2.75-2.63 (m, 2H), 2.41 (dd, J=15.5, 4.9 Hz, 1H), 2.31 (dd, J=15.5, 8.4 Hz, 1H), 1.55 (m, 1H), 1.44-1.31 (m, 2H), 0.81 (d, J=6.6 Hz, 3H), 0.79 (d, J=6.6 Hz, 3H). $^{13}$C NMR (100 MHz, DMSO-d$_6$) δ 200.3, 172.5, 171.7, 171.6, 156.4, 145.6 145.5, 144.4, 144.1, 141.1, 137.3, 129.3, 128.7, 128.1, 127.5, 126.9, 125.7, 125.18, 120.5, 66.0, 61.2, 53.3, 49.7, 47.1, 46.3, 31.6, 24.5, 23.6, 21.8. HRMS m/z calcd for C$_{48}$H$_{48}$N$_4$O$_6$S [MH$^+$] 809.3295, found 809.4387. H-Leu-Asn-Phe-SH (A9). To a solution of SB5 (0.075 g, 0.093 mmol) in DMF (0.930 mL) was added DBU (0.028 g, 0.19 mmol) and the solution was stirred under argon. After 30 minutes, the solution was diluted with DMF to a total volume of 3 mL, and purified by semi-preparative HPLC to give the TFA salt of A9 as a fluffy white solid (0.052 g, 88% yield). HPLC: gradient 5 to 100% B/A over 20 min, 0.6 mL/min t$_R$: 10.5 min. HRMS m/z calcd for C$_{19}$H$_{25}$N$_4$O$_4$S [MH$^+$] 409.1831, found 409.2431. Due to the instability of A9, it was used directly in the subsequent ligation reactions and analytical samples of the purified products were prepared and analyzed immediately.

Synthesis of H-Val-Gln-Lys-Asp(SH)-Val-Thr-Ser-OMe (A12) (SEQ ID NO: 8).

Boc-Val-Gln(Tr)-Lys(Boc)-Asp(OAll)-Val-Thr($^t$Bu)-Ser($^t$Bu)-OH (SB6) (SEQ ID NO: 12). A solution of Fmoc-Ser($^t$Bu)-OH (2.02 g, 5.27 mmol)+DIEA (1.4 mL, 8.0 mmol) in DCM (15 mL) was added to 2-chlorotrityl resin (1.50 g, 0.70 mmol/g, 1.1 mmol) in a peptide synthesis vessel. After 1 h, the resin was rinsed with DCM and then treated with 16/3/1 DCM:DIEA:MeOH (10 mL v/v/v) to cap any unreacted loading sites. After 1 h, the resin was rinsed sequentially as follows: 3 times with DCM, 2 times with DMF, 3 times with DCM, and 3 times with MeOH to shrink the beads. The resin was dried in vacuo overnight, and the loading capacity of the Fmoc-Ser($^t$Bu)-Resin was estimated gravimetrically or by performing a Fmoc deprotection and measuring the Fmoc-piperidine adduct yield spectrophotometrically. Based on this loading capacity determination, Boc-Val-Gln(Tr)-Lys(Boc)-Asp(OAll)-Val-Thr($^t$Bu)-Ser($^t$Bu)-Resin (SEQ ID NO: 12) was assembled from Fmoc-Ser(tBu)-Resin (738 mg, 0.574 mmol/g, 0.424 mmol) using the standard SPPS protocols. The on-resin peptide was then agitated with 1:1:8 AcOH/TFE/DCM (10 mL/1 g resin) to obtain S6 (422 mg, 73% crude yield, 83% pure by HPLC analysis). The product was used without further purification. HPLC: isocratic 80% B/A 0.7 mL/min t$_R$: 6.0 min. $^1$H NMR (600 MHz, CDCl$_3$) [the sample is crude and diagnostic peaks are listed only]: δ 7.28-7.17 (aromatic, 15H), 5.85 (bm, 1H), 5.25 (m, 1H), 5.17 (d, J=9.9 Hz, 1H) 1.42 (s, 9H), 1.32 (s, 9H), 1.27 (s, 9H), 1.16 (s, 9H) 1.12-1.03 (4H), 0.97-0.83 (15H). LRMS m/z calcd for C$_{72}$H$_{108}$N$_9$O$_{17}$ [MH$^+$] 1370.7. found 1370.3; LRMS m/z calcd for C$_{72}$H$_{107}$N$_9$NaO$_{17}$ [MNa$^+$] 1392.8. found 1392.9.

Boc-Val-Gln(Tr)-Lys(Boc)-Asp-Val-Thr($^t$Bu)-Ser($^t$Bu)-OMe (SB7). Using a modified version of a known procedure, N,N-nitrosomethylurea (300 mg, 2.94 mmol) was slowly added, with gentle swirling, to an ice-cold bi-phasic mixture of Et$_2$O (5 mL) over a solution of KOH (1.2 g) in water (2 mL). The yellow ether layer was decanted by pipette, and the aq. layer was further extracted by gently swirling with additional Et$_2$O (5 mL). The ice-cold ether layers were combined and kept at or below 0° C. for all subsequent manipulations. To an ice-cold solution of 56 (298 mg) in DCM (5 mL), the ethereal diazomethane solution was added dropwise until the yellow color of diazomethane persisted. The solution was stirred at 0° C. for 30 minutes, then the diazomethane was quenched with a few drops of AcOH, and the solvent was removed by rotary evaporation. The product was precipitated from Et$_2$O/hexanes, and the solvent was removed in mum to afford crude methyl ester (HPLC: isocratic 80% B/A over 15 min, 0.7 mL/min t$_R$: 13.6 min). The crude methyl ester was re-dissolved in DCM (20 mL) and the reaction vessel was flushed with argon. The stirring solution was charged with Pd(Ph$_3$P)$_4$ (25 mg, 10 mol %) and Et$_3$SiH (350 uL, 10 equiv.) and covered in foil. After 1 h, the solvent was removed by rotary evaporation and the reaction mixture was purified by semi-preparative HPLC to afford pure SB7 (156 mg, 54% yield over 15 steps).[8] HPLC: isocratic 80% B/A over 15 min, 0.7 mL/min h$_r$: 5.8 min. HRMS m/z calcd for C$_{70}$H$_{105}$N$_9$NaO$_{17}$ [MNa$^+$] 1366.7628, found 1367.0284.

Boc-Val-Gln(Tr)-Lys(Boc)-Asp(STmb)-Val-Thr($^t$Bu)-Ser($^t$Bu)-OMe (SB9).

To a stirring solution of SB7 (120 mg, 88 μmol) in DMF (0.200 mL) was sequentially added DIC[9] (28 μL, 0.18 mmol), SB8 (38 mg, 0.18 mmol), and DMAP (0.101 M in DMF, 88 μL, 8.8 nmol). After 18 h, the reaction mixture was directly purified by semi-preparative HPLC[11] to afford pure SB9 (88 mg, 65% yield) and a small amount of recovered starting material S7 (10 mg, 8%). HPLC: isocratic 80% B/A over 15 min, 0.7 mL/min t$_R$: 13.1 min. $^1$H NMR (600 MHz, CDCl$_3$) δ 8.62 (bs, 1H), 7.89 (d, J=8.4 Hz, 1H), 7.59 (d, J=7.6 Hz, 1H), 7.29-7.21 (aromatic, 15H) 7.00 (d, J=5.8 Hz, 1H), 6.91 (s, 1H), 6.06 (s, 2H), 4.88-4.85 (2H), 4.70 (d, J=8.5 Hz, 1H), 4.51 (bs, 1H), 4.40 (dd, J=6.0 Hz, 3.8 Hz, 1H), 4.23 (bs, 1H), 4.19-4.11 (4H), 3.94 (bm, 1H), 3.82 (dd, J=9.0, 3.2 Hz, 1H), 3.79 (s, 3H), 3.75 (app. s, overlapped MeO—, 6H), 3.71 (s, 3H), 3.52 (dd, J=8.9, 3.2 Hz, 1H), 3.21 (dd, J=16.8, 3.2 Hz, 1H), 3.16-2.99 (m, 3H), 2.70 (dd, J=15.6, 7.6 Hz, 1H), 2.33 (dd, J=16.4, 8.5 Hz, 1H), 2.23 (dd, J=13.6, 6.1 Hz, 1H), 2.16 (m, 1H), 2.00-1.80 (m, 2H), 1.42 (s, 9H), 1.36-1.30 (3H) 1.29 (s, 9H), 1.27 (s, 9H), 1.14-1.07 (11H), 0.92 (app. d, J=6.7 Hz, 6H), 0.81 (d, J=6.9 Hz, 3H), 0.69 (d, J=6.6 Hz, 3H). HRMS m/z calcd for C$_{80}$H$_{117}$N$_9$NaO$_{19}$S [MNa$^+$] 1562.8286, found 1563.0453.

H-Val-Gln-Lys-Asp(SH)-Val-Thr-Ser-OMe (A12). Solid SB9 (60 mg, 39 μmol) was dissolved in an ice-cold degassed cocktail of TFA (0.65 mL), DCM (0.20 mL) and Et$_3$SiH (0.25 mL) and stirred at ambient temperature under argon. After 3.5 h, the reaction was diluted with water (2 mL), extracted with Et$_2$O (2×1 mL), and the aq. layer was purified by semi-preparative HPLC to afford A12 (23 mg, 57% yield) as a fluffy white solid. Due to the instability of A12, it was used directly in the subsequent ligation reactions and analytical samples of the purified products were prepared and analyzed immediately. HPLC: gradient 5 to 100% B/A over 20 min, 0.6 mL/min t$_R$: 7.0 min. LRMS m/z calcd for C$_{33}$H$_{60}$N$_9$O$_{12}$S [MH$^+$] 806.4, found 806.5. HRMS m/z calcd for C$_{33}$H$_{60}$N$_9$O$_{12}$S [MH$^+$] 806.4002, found 806.5060; m/z calcd for C$_{33}$H$_{59}$N$_9$NaO$_{12}$S [MNa$^+$] 828.4003, found 828.4948.

Synthesis of H-Val-Gln-Lys-Asi-Val-Thr-Ser-OMe (SB10).

H-Val-Gln-Lys-Asi-Val-Thr-Ser-OMe (SB10). To a stirring solution of SB7 (5 mg, 4 μmol) in DMF (0.200 mL) was sequentially added DIC (1.4 μL, 15 μmol) and DMAP (7.4 μL, 0.10 M in DMF, 0.74 μmol). After 3 days, HPLC analysis had shown the complete consumption of SB7 to give the corresponding fully protected aspartimide (identified by HPLC and LRMS analysis: HPLC: isocratic 80% B/A, t$_R$: 10.1 min; LRMS m/z calcd for C70H$_{103}$N$_9$O$_{16}$ [MNa$^+$] 1348.8, found 1348.9). The excess DIC was quenched with water (0.500 mL). After the resulting white suspension was stirred for 1 h at rt, the reaction mixture had solvent removed under reduced pressure, and the residue was dissolved in an ice-cold cocktail of TFA (0.65 mL), DCM (0.20 mL) and Et$_3$SiH (0.25 mL) and stirred at ambient temperature for 4 h. At this time, the reaction was diluted with water (1 mL), extracted by Et$_2$O (1 mL), and the aq. layer was purified by semi-preparative HPLC to afford pure SB10 (3 mg, 81% yield). HPLC: gradient 5 to 100% B/A over 20 min, 0.6 mL/min t$_R$: 7.5 min. $^1$H NMR (600 MHz, DMSO-d$_6$) δ 8.70 (d, J=7.5 m/z, 1H), 8.54 (d, J=7.9 Hz, 1H), 8.23 (d, J=8.4 Hz, 1H), 8.10 (d, J=7.5 Hz, 1H), 8.10-8.02 (3H), 7.73 (d, J=8.4 Hz, 1H), 7.61 (bm, 3H), 7.21 (s, 1H), 6.83 (s, 1H), 5.09 (t, J=5.6 Hz, 1H), 4.87 (d, J=5.1 Hz, 1H), 4.40 (dd, J=15.0, 7.9 Hz, 1H), 4.33 (m, 3H), 4.22-4.18 (overlapping split peaks, 2H), 3.84 (m, 1H), 3.71 (m, 1H), 3.60 (app s, 5H), 2.97 (dd, J=17.4, 9.3 Hz, 1H), 2.70 (bs, 2H), 2.65-2.50 (3H), 2.09 (t, J=8.2 Hz, 2H), 2.00 (td, J=13.5, 6.8 Hz, 1H), 1.87 (dt, J=22.3, 7.3 Hz, 1H), 1.76 (tt, J=12.5, 6.1 Hz, 1H), 1.63 (bm, 3H), 1.48 (bm, 3H), 1.26 (s, 2H), 1.00 (d, J=6.4 Hz, 3H), 0.95 (d, J=6.6 Hz, 3H), 0.90 (d, J=2.2 Hz, 3H), 0.89 (d, J=2.2 Hz, 3H), 0.79 (d, J=6.6 Hz, 3H). HRMS m/z calcd for C$_{33}$H$_{60}$N$_9$O$_{12}$S [MH$^+$] 772.4207, found 772.4615; m/z calcd for C$_{33}$H$_{59}$N$_9$NaO$_{12}$S [MNa$^+$] 794.4126, found 794.4558.

General Ligation Procedure.

To a solution of aq. Cu(OAc)$_2$ (1.0 equiv.) and HOBt (2.0 equiv.) In aq. DMF (final reaction concentration of 0.05 M) was added peptide thioacid (1.0 equiv.) followed immediately by glycosyl amine (4.0 equiv.). After thirty minutes, the solution was diluted with water (volume equivalent to the reaction volume). The mixture was aged for 15 minutes allowing a precipitate to form. The heterogeneous mixture was then filtered through a 0.2 μm syringe filter and the filtrate purified by semi-preparative HPLC (conditions specified below) to give the product (isolated yield specified). The isolated products were analyzed by analytical HPLC, $^1$H NMR, and HRMS.

Cbz-Gly-Ac$_3$GlcNAc (A6). A$_5$ (0.0400 g, 0.178 mmol) was coupled to A4 (0.246 g, 0.710 mmol) following the general ligation protocol. The reaction was partitioned between EtOAc (3×15 mL) and water (3 mL). The combined organic extracts were washed with sequentially with water (2×5 mL) and brine (5 mL) then dried (MgSO$_4$) and filtered. The solvent was removed in vacuo and the crude residue was purified by flash chromatography using 5% MeOH/DCM as the eluent to give A6 as the product as a hydroscopic white solid (0.086 g, 90% yield). R$_f$ 0.28 (5% MeOH/DCM), $^1$H NMR (400 MHz, CDCl$_3$) δ 7.50 (d, J=8.2 Hz, 1H), 7.35-7.21 (m, 5H), 6.17 (d, J=8.1 Hz, 1H), 5.36 (br t, J=5.4 Hz, 1H), 5.07 (s, 2H), 5.03 (m, 3H), 4.22 (dd, J=12.5, 4.3 Hz, 1H), 4.15-4.04 (m, 1H), 4.01 (dd, J=12.5, 2.1 Hz, 1H), 3.79 (dd, J=10.8, 5.8 Hz, 2H), 3.73 (ddd, J=9.8, 4.1, 2.3 Hz, 1H), 2.01 (s, 3H), 1.99 (s, 3H), 1.97 (s, 3H), 1.88 (s, 3H). HRMS m/z calcd for C$_{24}$H$_{32}$N$_3$O$_{11}$ [MH$^+$] 538.2037, found 538.2020; m/z calcd for C$_{24}$H$_{32}$N$_3$O$_{11}$ [MNa$^+$] 560.1856, found 560.1851; m/z calcd for C$_{24}$H$_{32}$N$_3$O$_{11}$ [MK$^+$] 576.1596 found 576.1595.

Cbz-Gly-GlcNAc (A8). A7 (19 mg, 0.086 mmol) was coupled to A5 (5.0 mg, 0.022 mmol) following to the general ligation protocol to give pure A8 (8.6 mg, 94% yield) as a fluffy white solid. HPLC: gradient 5 to 100% B/A over 20 min, 0.6 mL/min t$_R$: 9.3 min. $^1$H NMR (600 MHz, DMSO-d$_6$) δ 7.99 (d, J=8.6 Hz, 1H), 7.88 (d, J=8.6 Hz, 1H), 7.49 (t, J=6.2 Hz, 1H), 7.41-7.33 (m, 4H), 7.31 (t, J=6.9 Hz, 1H), 5.04 (s, 2H), 4.74 (t, J=9.1 Hz, 1H), 3.64 (d, J=11.1 Hz, 1H), 3.59 (d, J=6.3 Hz, 1H), 3.54 (AB q, J=9.8 Hz, 2H), 3.48 (d, J=6.1 Hz, 1H), 3.47-3.41 (m, 2H), 3.34-3.30 (m, 1H), 3.13-3.07 (m, 2H), 1.82 (s, 3H). HRMS m/z calcd for C$_{18}$H$_{25}$N$_3$O$_8$ [MH$^+$] 412.1720, found 412.1700; m/z calcd for C$_{18}$H$_{25}$N$_3$O$_8$ [MNa$^+$] 434.1539. found 434.1518, m/z calcd for C$_{18}$H$_{25}$N$_3$O$_8$ [MK$^+$] 450.1279, found 450.1282.

H-Leu-Asn-Phe-Ac$_3$GlcNAc (A10). A4 (9.3 mg, 0.027 mmol) was coupled to A9 (3.5 mg, 6.7 nmol) following the general ligation protocol to give A10 (3.5 mg, 73% yield) as a fluffy white solid. HPLC: gradient 5 to 100% B/A over 20 min, 0.6 mL/min t$_R$: 10.9 min. $^1$H NMR (600 MHz, DMSO-d$_6$) δ 8.63 (d, J=9.0 Hz, 1H), 8.57 (d, J=7.9 Hz, 1H), 8.07 (d, J=8.1 Hz, 1H), 8.02 (br s, 2H), 7.89 (d, J=9.1 Hz, 1H), 7.42 (s, 1H), 7.21-7.20 (m, 3H), 7.16 (td, J=5.6, 2.7 Hz, 1H), 6.93 (br s, 1H), 6.52 (s, 1H), 5.17 (t, J=9.4 Hz, 1H), 5.12 (t, J=9.9 Hz, 1H), 4.82 (t, J=9.8 Hz, 1H), 4.60 (q, J=7.1 Hz, 1H), 4.38 (td, J=8.9, 4.1 Hz, 1H), 4.18 (dd, J=12.4, 4.4 Hz, 1H), 3.99-3.93 (m, 2H), 3.82 (ddd, J=10.1, 4.5, 2.5 Hz, 1H), 3.73-3.70 (m, 1H), 3.01 (dd, J=14.1, 4.0 Hz, 1H), 2.75 (dd, J=14.0, 9.4 Hz, 1H), 2.40-2.34 (m, 1H), 1.99 (s, 3H), 1.95 (s, 3H), 1.90 (s, 3H), 1.75 (s, 3H), 1.59 (dt, J=13.2, 6.6 Hz, 1H), 1.45-1.40 (m, 2H), 1.02 (d, J=6.1 Hz, 1H), 0.85 (d, J=6.5 Hz, 3H), 0.83 (d, J=6.5 Hz, 3H). HRMS m/z calcd for $C_{33}H_{48}N_6O_{12}$ [MNa$^+$] 743.3228, found 743.3250.

H-Leu-Asn-Phe-GlcNAc (A11). A7 (10 mg, 0.045 mmol) was coupled to A9 (6.0 mg, 0.011 mmol) following the general ligation protocol to give A11 (5.5 mg, 81% yield) as a fluffy white solid. HPLC: gradient 5 to 100% B/A over 20 min, 0.6 mL/min $t_R$: 8.5 min. $^1$H NMR (600 MHz, DMSO-d6) δ 8.59 (d, J=7.7 Hz, 1H), 8.14 (d, J=8.8 Hz, 1H), 8.07 (d, J=8.2 Hz, 2H), 8.04 (s, 2H), 7.85 (s, 1H), 7.40 (s, 1H), 7.25-7.21 (m, 4H), 7.19-7.16 (m, 1H), 6.94 (s, 1H), 5.00 (s, 1H), 4.81 (t, J=9.2 Hz, 1H), 4.63 (q, J=7.6 Hz, 1H), 4.59-4.56 (m, 1H), 4.31 (td, J=9.1, 4.0 Hz, 1H), 3.72 (s, 1H), 3.66 (d, J=11.2 Hz, 2H), 3.58 (q, J=9.7 Hz, 1H), 3.11 (s, 2H), 3.02 (dd, J=14.1, 3.8 Hz, 1H), 2.77 (dd, J=14.0, 9.5 Hz, 1H), 2.61 (t, J=7.9 Hz, 2H), 2.41-2.35 (m, 2H), 1.81 (s, 3H), 1.63 (dt, J=13.5, 6.8 Hz, 1H), 1.46 (t, J=7.1 Hz, 2H), 0.85 (d, J=6.5 Hz, 3H), 0.83 (d, J=6.5 Hz, 3H). HRMS m/z calcd for $C_{27}H_{42}N_6O_9$ [MNa$^+$] 617.2911, found 617.2897.

H-Val-Gln-Lys-Asp[(OAc)$_3$GlcNAc]-Val-Thr-Ser-OMe (A13). A4 (6.7 mg, 0.019 mmol) was coupled to A12 (4.9 mg, 4.7 μmol) following the general ligation protocol to give A13 (3.5 mg, 55% yield) as a fluffy white solid. HPLC: isocratic 10% B/A over 2 min, then gradient 10 to 60% B/A over 23 min, 0.6 mL/min $t_R$: 11.9 min. $^1$H NMR (600 MHz, DMSO-d$_6$) δ 8.62 (d, J=9.3 Hz, 1H), 8.51 (br s, 1H), 8.33 (d, J=8.6 Hz, 1H), 8.13 (m, 1H), 8.03-7.97 (1H), 7.91-7.84 (2H), 7.68-7.53 (3H), 7.30-7.25 (2H), 7.17 (dd, J=18.1, 6.5 Hz, 1H), 6.84-6.80 (2H), 5.15 (t, J=10.0 Hz, 1H), 5.10 (m, 2H), 5.02 (d, J=4.9 Hz, 1H), 4.83 (t, J=9.7 Hz, 1H), 4.62 (m, 1H), 4.35 (m, 2H), 4.31-4.24 (3H), 4.19 (dd, J=12.7, 3.9 Hz, 1H), 3.94 (m, 2H), 3.87 (dd, J=19.5, 9.5 Hz, 1H), 3.80 (m, 1H), 3.76-3.71 (2H), 3.62 (s, 3H), 2.70 (bm, 4H), 2.12 (m, 4H), 1.99 (s, 3H), 1.96 (s, 3H), 1.91 (s, 3H), 1.75 (s, 3H), 1.61 (m, 2H), 1.48 (bm, 4H), 1.33-1.21 (5H), 1.12-1.02 (d overlapped with bm, 6H), 0.91 (d, J=6.7 Hz, 6H), 0.83 (d, J=6.8 Hz, 6H), 0.79 (d, J=6.7 Hz, 6H). HRMS m/z calcd for $C_{47}H_{80}N_{11}O_{20}$ [MH$^+$] 1118.5503, found 1118.6908; m/z calcd for $C_{47}H_{80}N_{11}O_{20}$ [MNa$^+$] 1140.5504, found 1140.6849.

H-Val-Gln-Lys-Asp-[GlcNAc]-Val-Thr-Ser-OMe (A14). A7 (4.3 mg, 0.020 mmol) was coupled to A12 (5.0 mg, 4.9 μmol) following the general ligation protocol to give A14 (3.9 mg, 65%) as a fluffy white solid. HPLC: gradient 5 to 100% B/A over 20 min, 0.6 mL/min $t_R$: 6.1 min. $^1$H NMR (600 MHz, DMSO-d$_6$) δ 8.52 (d, J=7.9 Hz, 1H), 8.25 (d, J=7.6 Hz, 1H), 8.19 (d, J=9.0 Hz, 1H), 8.13 (d, J=8.0 Hz, 1H), 8.02 (s, 2H), 7.98 (d, J=7.7 Hz, 1H), 7.86 (d, J=8.3 Hz, 1H), 7.76 (d, J=8.7 Hz, 1H), 7.64-7.58 (m, 4H), 7.27 (s, 1H), 6.82 (s, 1H), 5.08 (t, J=5.6 Hz, 1H), 5.01 (d, J=4.8 Hz, 1H), 5.00 (d, J=4.7 Hz, 1H), 4.96 (d, 5.3 Hz, 1H), 4.76 (t, J=9.3 Hz, 1H), 4.56 (t, J=6.2 Hz, 2H), 4.37-4.30 (m, 3H), 4.26 (dd, J=8.5, 4.5 Hz, 2H), 4.23 (dd, J=9.0, 6.0 Hz, 1H), 3.93-3.89 (m, 1H), 3.71 (dt J=10.5, 4.8 Hz, 1H), 3.63 (dd, J=11.9, 5.8 Hz, 1H), 3.50 (q, J=9.6 Hz, 1H), 3.43-3.37 (m, 1H), 3.07-3.03 (m, 2H), 2.69 (s, 2H), 2.64-2.57 (m, 2H), 2.38-2.31 (m, 2H), 2.18-2.05 (m, 2H), 1.99 (m, J=2H), 1.89-1.82 (m, 1H), 1.78 (s, 3H), 1.62 (s, 1H), 1.46 (dd, J=12.2, 6.8 Hz, 1H), 1.24 (m, 1H), 1.05 (d, J=6.2 Hz, 2H), 0.89 (d, J=6.8 Hz, 6H). 0.81 (d, J=6.8 Hz, 3H), 0.78 (d, J=6.7 Hz, 3H). HRMS m/z calcd for $C_{47}H_{80}N_{11}O_{20}$ [MNa$^+$] 1014.5005, found 1014.5091.

H-Val-Gln-Lys-Asp-[GlcNAcβ-4GlcNAc]-Val-Thr-Ser-OMe (A16).

A15 (7.8 mg, 0.018 mmol) was coupled to A12 (4.8 mg, 4.6 μmol) following the general ligation protocol to give A16 (3.5 mg, 53%) as a fluffy white solid. HPLC: gradient 5 to 40% B/A over 15 min, 0.6 mL/min $t_R$: 7.9 min. $^1$H NMR (600 MHz, DMSO-d$_6$) δ 8.58 (d, J=8.1 Hz, 1H), 8.32 (t, J=9.3 Hz, 1H), 8.19 (d, J=7.9 Hz, 1H), 8.13-8.03 (m, 3H). 7.94-7.90 (m, 2H), 7.77 (d, J=9.3 Hz, 1H), 7.71-7.62 (m, 3H), 7.33 (s, 1H), 6.90 (s, 1H), 5.14 (q, J=4.8 Hz, 1H), 5.07 (dd, J=18.1, 5.1 Hz, 1H), 4.88-4.83 (m, 1H), 4.76 (t, J=4.9 Hz, 1H), 4.64 (t, J=5.3 Hz, 1H), 4.44-4.38 (m, 2H), 4.35-4.28 (m, 2H), 3.98 (d, J=4.9 Hz, 1H), 3.83-3.75 (m, 1H), 3.67 (s, 3H), 3.65-3.61 (m, 2H), 3.57-3.53 (m, 1H), 3.48 (t. J=9.3 Hz, 1H), 2.80-2.73 (bm, 2H), 2.24-2.12 (bm, 3H), 2.10-2.01 (bm, 3H), 1.87 (s, 3H), 1.85 (s, 3H), 1.73-1.65 (bm, 1H), 1.57-1.50 (bm, 3H), 1.37-1.28 (m, 3H), 1.12 (d, J=6.2 Hz, 3H), 0.96 (d, J=6.7 Hz, 6H), 0.88 (d, J=6.6 Hz, 3H), 0.85 (d, J=6.7 Hz, 3H). HRMS m/z calcd for $C_{47}H_{80}N_{11}O_{20}$ [MNa$^+$] 1217.5980, found 1217.7001; m/z calcd for $C_{47}H_{80}N_{11}O_{20}$ [MK$^+$] 1233.5980, found 1233.6913.

REFERENCES AND NOTES FOR BACKGROUND AND EXAMPLE 2

(1) Dwek, R. A. *Chem. Rev.* 1996, 96, 683.
(2) Gamblin, D. P.; Scanlan, E. M.; Davis, B. G. *Chem. Rev.* 2009, 109, 131.
(3) (a) Lauc, G.; Zoldos, V. *Medical Hypotheses* 2009, 73, 510. (b) Lauc, G.; Zoldos, V. *Molecular Biosystems* 2010, 6, 2373.
(4) Kannagi, R.; Yin, J.; Miyazaki, K.; Izawa, M. *Biochim. Biophyc. Acta* 2008, 1780, 525.
(5) Rich, J. R.; Withers, S. G. *Nature Chemical Biology* 2009, 5, 206.
(6) Kent, S. B. H. *Chem. Soc. Rev.,* 2009, 38, 338.
(7) Piontek, C.; Ring, P.; Harjes, O.; Heinlein, C.; Mezzato, S.; Lombana, N.; Pohner, C.; Püttner, M.; Silva, D. V.; Martin, A.; Schmidt, F. X.; Unverzagt, C. *Angew. Chem. Int. Ed.* 2009, 48, 1936; Piontek, C.; Silva, D. V.; Heinlein, C.; Pöhner, C.; Mezzato, S.; Ring, P.; Martin, A.; Schmidt, F. X.; Unverzagt, C. *Angew. Chem. Int. Ed.* 2009, 48, 1941. (b) Aussedat, B.; Fasching, B.; Johnston, E.; Sane, N.; Nagorny, P.; Danishefsky, S. J. *J. Am. Chem. Soc.* 2012, 134, 3532. (c) Sakamoto, I.; Tezuka, K.; Fukae, K.; Ishii, K.; Tadurur, K.; Maeda, M.; Ouchi, M.; Yoshida, K.; Nambu, Y.; Igarashi, J.; Hayashi, N.; Tsuji, T.; Kajihara, Y. *J. Am. Chem. Soc.* 2012, 134, 5428.
(8) (a) Anisfeld, S. T. and Lansbury Jr, P. T. *J. Org. Chem.* 1990, 55, 5560. (b) Cohen-Anisfeld, S. T.; Lansbury Jr, P. T. *J. Am. Chem. Soc.* 1993, 115, 10531.
(9) Wang, P.; Li, X.; Zhu, J.; Chen, J.; Yuan, Y.; Wu, X.; Danishefsky, S. J. *J. Am. Chem. Soc.* 2011, 133, 1597.
(10) Kaneshiro, C. M.; Michael, K. *Angew. Chem. Int. Ed.* 2006, 45, 1077.
(11) (a) Ullmann, V.; Radisch, M.; Boos, I.; Freund, J.; Pohner, C.; Schwarzinger, S.; Unverzagt, C., *Angew. Chem. Int. Ed.* 2012, doi: 10.1002/anie.201204272. (b) Wang, P.; Aussedat, B.; Vohra, Y.; Danishefsky, S. J., *Angew. Chem. Int. Ed.* 2012, doi: 10.1002/anie.201205038.
(12) (a) Davis and coworkers reported the coupling of GlcNAcβ-N$_3$ and Fmoc-Ser-Asp(OBt)-Leu-Thr-NH$_2$ using the Staudinger reaction: Doores, K. J.; Mimura, Y.;

Dwek, R. A.; Rudd, P. M.; Elliott, T.; Davis, B. G. *Chem. Commun.* 2006, 1401. (b) Damkaci, F.; DeShong, P., *J. Am. Chem. Soc.* 2003, 125, 4408

(13) Dyer, F. B.; Park, C.-M.; Joseph, R.; Garner, P. *J. Am. Chem. Soc.* 2011, 133, 20033.

(14) Legler, G. *Biochim. Biophys. Acta,* 1978, 524, 94.

(15) Glycosylamine 4 was prepared from commercially available glucosamine hydrochloride (1a. NaOMe/MeOH; 1b. $Ac_2O$ 0° C. to rt, 92% yield; 2. AcCl, rt, 65% yield; 3. $NaN_3$, DMF, 70° C., 96% yield; 4. $H_2$ Pd/C, EtOAc, rt, 90% yield) using a known method: Cunha, A.; Pereira, L. c.; de Souza, R.; de Souza, M. C. I.; Ferreira, V. *Nucleosides, Nucleosides Nucleic Acids,* 2001, 20, 1555.

(16) Thioacid 5 was prepared from commercially available Cbz-Gly-OH (1. TrtSH, EDC, DMAP, $CH_2Cl_2$, rt, 90% yield; 2. TFA, $Et_3SiH$, $CH_2Cl_2$, rt, 85% yield) using a known method: Crich, D.; Sharma, I. *Angew. Chem. Int. Ed.* 2009, 48, 7591.

(17) While our work was already in progress, Gopi and coworkers reported the facile, Cu(II)-promoted coupling of thioacids and amines in MeOH. The method was applied to the synthesis of fully-protected peptides. They also showed that this amidation was catalyzed by in situ generated copper sulfide. Mali, S. M.; Jadhav, S. V.; Gopi, H. N. *Chem. Commun.* 2012, 48, 7085-7087.

(18) Isbell, H. S.; Frush, H. J. *J. Org. Chem.* 1958, 23, 1309.

(19) The benefit of adding Cu(II) salts together with HOBt or $Cu(OBt)_2$ to standard peptide coupling reactions in order to suppress racemization has been known for some time: (a) Miyazawa, T.; Otomatsu, T.; Fukui, Y.; Yamada, T.; Kuwata, S. *Int. J. Peptide Protein Res.* 1992, 39, 308. (b) Gibson, F. S.; Rapoport, H. *J. Org. Chem.* 1995, 60, 2615. (c) Ryadnov, M. G.; Klimenko, L. V.; Mitin, Y. V. *J. Peptide Res.* 1999, 53, 322. (d) Van den Nest, W.; Yuval, S.; Albericio, F. *J. Peptide Sci.* 2001, 7, 115.

(20) Kiyozumi, M.; Kato, K.; Komori, T.; Yamamoto, A.; Kawasaki, T.; Tsukamoto, H. *Carbohyd. Res.* 1970, 14, 355.

(21) Known compound Boc-Phe-SFm was elongated to Fmoc-Leu-Asn-Phe-SFm with HATU/Boc chemistry then globally deprotected with DBU and purified by HPLC. See: Wu, W.; Zhang, Z.; Liebeskind, L. S., *J. Am. Chem. Soc.* 2011, 133, 14256.

(22) Lack of selectivity would lead to peptide coupling products of the type H-Leu-Asn-Phe-Leu-Asn-Phe-X (X=SH, OH, $Ac_3GlcNAc\beta$-NH), which were not detected in the crude reaction mixture.

(23) Synthesis of peptide thioacid 12: Boc-Val-Gln(Tr)-Lys(Boc)-Asp(OAll)-Val-Thr($^tBu$)-Ser($^tBu$) on 2-chlorotrityl resin was synthesized using standard Fmoc-based solid phase synthesis protocols. Conversion to 12 was accomplished in solution (1. AcOH/TFE/DCM to obtain Boc-Val-Gln(Tr)-Lys(Boc)-Asp(OAll)-Val-Thr($^tBu$)-Ser($^tBu$)-OH; 2. $CH_2N_2$; 3. $Pd(PPh_3)_4$/$pTolSO_2Na$; 4. DIC, cat. DMAP, HS-Tmb; 5. TFA global deprotection).

(24) Hackenberger, C. P. R.; O'Reilly, M. K.; Imperiali, B. *J. Org. Chem.* 2005, 70, 3574.

(25) This conclusion was confirmed by comparing with a genuine sample of the expected aspartimide.

(26) Pierce, J. G.; Parsons. T. F. *Ann. Rev. Biochem.* 1981, 50, 465.

(27) Kiyozumi, M.; Kato, K.; Komori, T.; Yamamoto, A.; Kawasaki, T.; Tsukamoto, H., *Carbohydrate Research* 1970, 14, 355-364.

(28) (a) Glycosylazide SB1 was prepared from commercially available glucosamine hydrochloride following a known protocol (1a. NaOMe/MeOH; 1b. $Ac_2O$ 0° C. to rt, 92% yield; 2. AcCl, rt, 65% yield; 3. $NaN_3$, DMF, 70° C., 96% yield). See Cunha, A.; Pereira, L.; de Souza, R.; de Souza, M. C.; Ferreira, V., *Nucleosides, Nucleotides & Nucleic Acids* 2001, 20, 1555-1569. (b) 1. Hong, S. Y.; Tobias, G.; Ballesteros, B.; El Oualid, F.; Errey, J. C.; Doores, K. J.; Kirkland, A. I.; Nellist, P. D.; Green, M. L. H.; Davis, B. G., *J. Am. Chem. Soc.* 2007, 129, 10966-10967.

(29) Amblard, M.; Fehrentz, J.-A.; Martinez, J.; Subra, G. *Mol. Biotechnol.* 2006, 33, 239-254.

(30) Amblard, M.; Fehrentz, J.-A.; Martinez, J.; Subra, G. *Mol. Blotechnol.* 2006, 33, 239-254.

(31) The synthesis of Boc-Phe-SFm was performed as reported. See: Wu, W.; Zhang, Z.; Liebeskind, L. S., *J. Am. Chem. Soc.* 2011, 133, 14256-14259.

(32) The production of diazomethane can be hazardous. Those unfamiliar with its use should read the following article for further safety information. Arndt, F. *Org. Syn.,* 1935, 15, 3.

(33) Arndt, F. *Org. Syn.,* 1935, 15, 48.

(34) Vetter, S. Synth. Comm. 1998, 28, 3219-3223.

(35) Compound SB9 was found to be unstable to silica gel and also unstable to normal solvent removal techniques. The lyophilization after HPLC purification was the only reliable way to recover pure SB9.

(36) All ligations were performed using stock solutions prepared from HOBt and $Cu(OAc)_2.H_2O$. Stock solutions for HOBt were all prepared at 2.00 M concentration in reagent grade DMF. Stock solutions of $Cu(OAc)_2$ were all prepared at 0.300 M concentration in deionized water using $Cu(OAc)_2.H_2O$.

(37) Crich, D.; Sharma, I. *Angew. Chem. Int. Ed.* 2009, 48, 7591-7593.

(38) The synthesis of chitobiosylamine was performed as reported: Hackenberger, C. P. R.; O'Reill, M. K.; Imperiali, B., *J. Org. Chem.* 2005, 70, 3574-3578.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

I claim:

1. A method of forming a glycosylated ligation product, comprising reacting the peptide thioacid H-Leu-Asn-Phe-SH with a compound that comprises a glycosylamine under conditions suitable for forming said ligation product.

2. The method of claim 1, wherein said conditions suitable for forming said ligation product are such that an amide bond is formed by displacement of SH of the thioacid by N of the glycosylamine, thereby forming said ligation product.

3. The method of claim 1, wherein said peptide thioacid does not contain a protecting group.

4. The method of claim 1, wherein said compound that comprises a glycosylamine is selected from the group consisting of a monosaccharide, a disaccharide, an oligosaccharide, a polysaccharide or a modified saccharide.

5. The method of claim 1, wherein said step of reacting is performed in the presence of Cu(II) ion.

6. The method of claim 1, wherein said step of reacting is carried out at ambient temperature.

* * * * *